United States Patent
Fujimura et al.

(10) Patent No.: US 8,742,023 B2
(45) Date of Patent: Jun. 3, 2014

(54) ABSORBENT RESIN PARTICLE, PROCESS FOR PRODUCING THE SAME, ABSORBER CONTAINING THE SAME, AND ABSORBENT ARTICLE

(75) Inventors: Takashi Fujimura, Tokyo (JP); Hidenobu Ishida, Tokyo (JP)

(73) Assignee: San-Dia Polymers, Ltd., Tokyo (JP)

( * ) Notice: Subject to any disclaimer, the term of this patent is extended or adjusted under 35 U.S.C. 154(b) by 202 days.

(21) Appl. No.: 13/142,098

(22) PCT Filed: Dec. 24, 2009

(86) PCT No.: PCT/JP2009/007174
§ 371 (c)(1),
(2), (4) Date: Aug. 3, 2011

(87) PCT Pub. No.: WO2010/073658
PCT Pub. Date: Jul. 1, 2010

(65) Prior Publication Data
US 2011/0301560 A1 Dec. 8, 2011

(30) Foreign Application Priority Data
Dec. 26, 2008 (JP) ................................. 2008-333207

(51) Int. Cl.
*C08F 8/00* (2006.01)

(52) U.S. Cl.
USPC ..................... 525/326.1; 525/329.7; 525/384; 502/402

(58) Field of Classification Search
USPC ..................... 525/326.1, 329.7, 384
See application file for complete search history.

(56) References Cited

U.S. PATENT DOCUMENTS

| | | | |
|---|---|---|---|
| 3,901,236 A * | 8/1975 | Assarsson et al. | 604/368 |
| 4,541,871 A * | 9/1985 | Obayashi et al. | 106/193.1 |
| 4,590,227 A | 5/1986 | Nakamura et al. | |
| 5,137,537 A * | 8/1992 | Herron et al. | 8/120 |
| 6,514,615 B1 | 2/2003 | Sun et al. | |

(Continued)

FOREIGN PATENT DOCUMENTS

| EP | 0 450 922 A2 | 10/1991 |
|---|---|---|
| EP | 0505163 A1 | 3/1992 |

(Continued)

OTHER PUBLICATIONS

Extended European Search Report dated Jul. 6, 2012, issued in corresponding European Patent Application No. 09834464.1 (4 pages).

*Primary Examiner* — Robert C Boyle
(74) *Attorney, Agent, or Firm* — Westerman, Hattori, Daniels & Adrian, LLP

(57) ABSTRACT

There is provided an absorbent resin particle having an absorption rate pattern where the rate is slow in the initial stage, moderate in the middle stage, and fast in the late stage, and there is also provided an absorbent article free from problems such as skin irritation by using the absorbent resin particle.

The present invention relates to an absorbent resin particle comprising a crosslinked polymer (A1) including, as an essential constituent unit, a water-soluble vinyl monomer (a1) and/or a hydrolyzable vinyl monomer (a2), and a crosslinking agent (b),
wherein, in a measurement method of swelled volume per 1 g of the absorbent resin particle against physiological saline, a ratio (t2/t1) of the time (t2) until swelled volume reaches 40 ml to the time (t1) until the swelled volume reaches 5 ml is 5 to 20.

15 Claims, 5 Drawing Sheets

(56) References Cited

U.S. PATENT DOCUMENTS

| | | | |
|---|---|---|---|
| 6,565,768 B1 * | 5/2003 | Dentler et al. | 252/194 |
| 2003/0118820 A1 | 6/2003 | Sun et al. | |
| 2003/0118821 A1 | 6/2003 | Sun et al. | |
| 2005/0101680 A1 | 5/2005 | Sun et al. | |
| 2005/0118423 A1 | 6/2005 | Adachi et al. | |
| 2006/0282052 A1 | 12/2006 | Saito et al. | |
| 2007/0185366 A1 | 8/2007 | Masuda et al. | |

FOREIGN PATENT DOCUMENTS

| | | |
|---|---|---|
| JP | 51-136588 A | 11/1976 |
| JP | 54-30710 B2 | 3/1979 |
| JP | 55-133413 A | 10/1980 |
| JP | 56-26909 A | 3/1981 |
| JP | 58-180233 A | 10/1983 |
| JP | 59-189103 A | 10/1984 |
| JP | 61-16903 A | 1/1986 |
| JP | 61-58658 A | 3/1986 |
| JP | 61-211305 A | 9/1986 |
| JP | 61-252212 A | 11/1986 |
| JP | 61-257235 A | 11/1986 |
| JP | 2001-200011 A | 7/2001 |
| JP | 2002-35580 A | 2/2002 |
| JP | 2003-503554 A | 1/2003 |
| JP | 2003-165883 A | 6/2003 |
| JP | 2003-225565 A | 8/2003 |
| JP | 2004-261796 A | 9/2004 |
| JP | 2005-75982 A | 3/2005 |
| JP | 2005-95759 A | 4/2005 |
| JP | 2005-97569 A | 4/2005 |
| JP | 3648553 B2 | 5/2005 |
| JP | 2006-131767 A | 5/2006 |
| JP | 2007-538110 A | 12/2007 |

* cited by examiner

ABSORBENT RESIN PARTICLE, PROCESS FOR PRODUCING THE SAME, ABSORBER CONTAINING THE SAME, AND ABSORBENT ARTICLE

TECHNICAL FIELD

The present invention relates to an absorbent resin particle, a process for producing the same, an absorber containing the same, and an absorbent article.

BACKGROUND ART

As an absorbent resin particle excellent in absorption rate, there is known an absorbent resin particle having a structure wherein a hydrophobic substance is contained in the inside of a crosslinked polymer (Patent Document 1).

Also, there is known an absorbent resin particle wherein powder flowability and the like are improved by attaching a hydrophobic substance on the surface of a crosslinked polymer (Patent Document 2).

However, in the conventional absorbent resin particles and water absorbers, an absorption rate with the passage of time after they come into contact with a liquid to be absorbed (hereinafter referred to as absorption rate pattern) is not appropriate. Specifically, the conventional absorbent resin particles include an absorbent resin particle (i) having an absorption rate pattern where the rate is fast in the early stage, moderate in the middle stage, and moderate in the late stage (the above mentioned absorbent resin particle of Patent Document 1) and an absorbent resin particle (ii) having an absorption rate pattern where the rate is slow in the early stage, moderate in the middle stage, and moderate in the late stage (the above-described absorbent resin particle of Patent Document 2).

When these absorbent resin particles are applied to absorbent articles (disposable diapers, etc.), in the absorbers used in the absorbent articles, absorption ratios of the absorbent resins become uneven depending on the portions of the absorbers and thus the absorbers cannot be effectively used, so that there tends to arise problems that portions on which the liquid to be absorbed remains are apt to occur or time during which the liquid not absorbed all over the absorber stays is prolonged.

Specifically, in the case where the above-described absorbent resin particle (i) is used, a liquid to be adsorbed is rapidly absorbed in the initial stage after the contact with the absorbent resin particle at the portions with which the liquid comes into contact. However, when the absorbent resin particle absorbs the liquid and swells to become a gel form, diffusion and absorption of unabsorbed liquid is prevented and, as a result, there occurs unevenness in the absorption ratio that the absorption ratio of the absorbent resin particle is high at the portions which come into contact with the liquid to be absorbed and the absorption ratio of the absorbent resin particle is low at peripheral portions thereof. Thus, at the portions which come into contact with the liquid to be absorbed, the liquid not absorbed is apt to remain.

On the other hand, in the case where the above-described absorbent resin particle (ii) is used, the liquid is only gradually absorbed after the contact with the absorbent resin particle at the portions with which the liquid to be adsorbed comes into contact and unabsorbed liquid diffuses into the inside of the absorber. As a result, the absorption ratio of the absorbent resin particle tends to be equal at the portions with which the liquid to be absorbed comes into contact and at peripheral portion thereof. However, since the absorption rate is wholly slow, the time during which the liquid not absorbed all over the absorber stays is prolonged.

In these absorbent resin particles, at the portions where the unabsorbed liquid remains or at the portions where the liquid stays for a long time, there is a problem that a trouble such as skin irritation tends to occur on the skin of a wearer who comes into contact with the portions.

BACKGROUND ART DOCUMENTS

Patent Documents

[Patent Document 1] JP-A-2005-097569
[Patent Document 2] JP-A-2004-261796

SUMMARY OF THE INVENTION

Problems that the Invention is to Solve

Absorbent articles (disposable diapers, etc.) in which conventional absorbent resin particles are employed cannot completely absorb a liquid and the unabsorbed liquid comes into contact with the skin of a wearer to tend to cause a trouble such as skin irritation. Accordingly, there have been strongly demanded absorbent articles that are free from a trouble such as skin irritation, and absorbent resin particles that can be used in such absorbent articles.

An object of the present invention is to provide an absorbent resin particle having a specific and suitable absorption rate pattern, that is, an absorbent resin particle having an absorption rate pattern where the rate is slow in the early stage, moderate in the middle stage, and fast in the late stage. Another object thereof is to provide an absorption article free from such problems as skin irritation by using the absorption resin particle.

Means for Solving the Problems

As a result of extensive studies for achieving the above objects, the present inventors found that an absorbent resin particle having a specific absorption rate pattern can solve the above problems and thus accomplished the invention.

That is, the gist of the absorbent resin particle of the invention is an absorbent resin particle comprising a crosslinked polymer (A1) including, as an essential constituent unit, a water-soluble vinyl monomer (a1) and/or a hydrolyzable vinyl monomer (a2) and a crosslinking agent (b), wherein, in a measurement method of swelled volume per 1 g of the absorbent resin particle against physiological saline, a ratio (t2/t1) of the time (t2) until swelled volume reaches 40 ml to the time (t1) until the swelled volume reaches 5 ml is 5 to 20.

The gist of the absorber of the invention is to comprise the above-described absorbent resin particle and a fibrous material.

The gist of the absorbent article of the invention is to comprise the above-described absorber.

The gist of the process for producing an absorbent resin particle is a process for producing an absorbent resin particle comprising:

a step of mixing and/or kneading a hydrophobic substance (C) with a hydrogel of a crosslinked polymer (A1) including, as an essential constituent unit, a water-soluble vinyl monomer (a1) and/or a hydrolyzable vinyl monomer (a2) and an internal crosslinking agent (b); and/or a step of obtaining a hydrogel of a crosslinked polymer (A1) by polymerizing a water-soluble vinyl monomer (a1) and/or a hydrolyzable vinyl monomer (a2) and an internal crosslinking agent (b) as an essential constituent unit in the presence of a hydrophobic substance (C), wherein, in a measurement method of swelled volume per 1 g of the absorbent resin particle against physiological saline, a ratio (t2/t1) of the time (t2) until swelled volume reaches 40 ml to the time (t1) until the swelled volume reaches 5 ml is 5 to 20.

Advantage of the Invention

The absorbent resin particle of the invention has a specific and suitable absorption rate pattern where the rate is slow in the initial stage, moderate in the middle stage, and fast in the late stage.

Therefore, when the absorbent resin particle of the invention is applied to absorbent articles (disposable diapers, sanitary napkin, etc.), unevenness in the absorption ratio is small, excellent absorption performance (absorption amount and absorption rate) is exhibited, and skin irritation is hard to occur.

MODE FOR CARRYING OUT THE INVENTION

Figure 1:
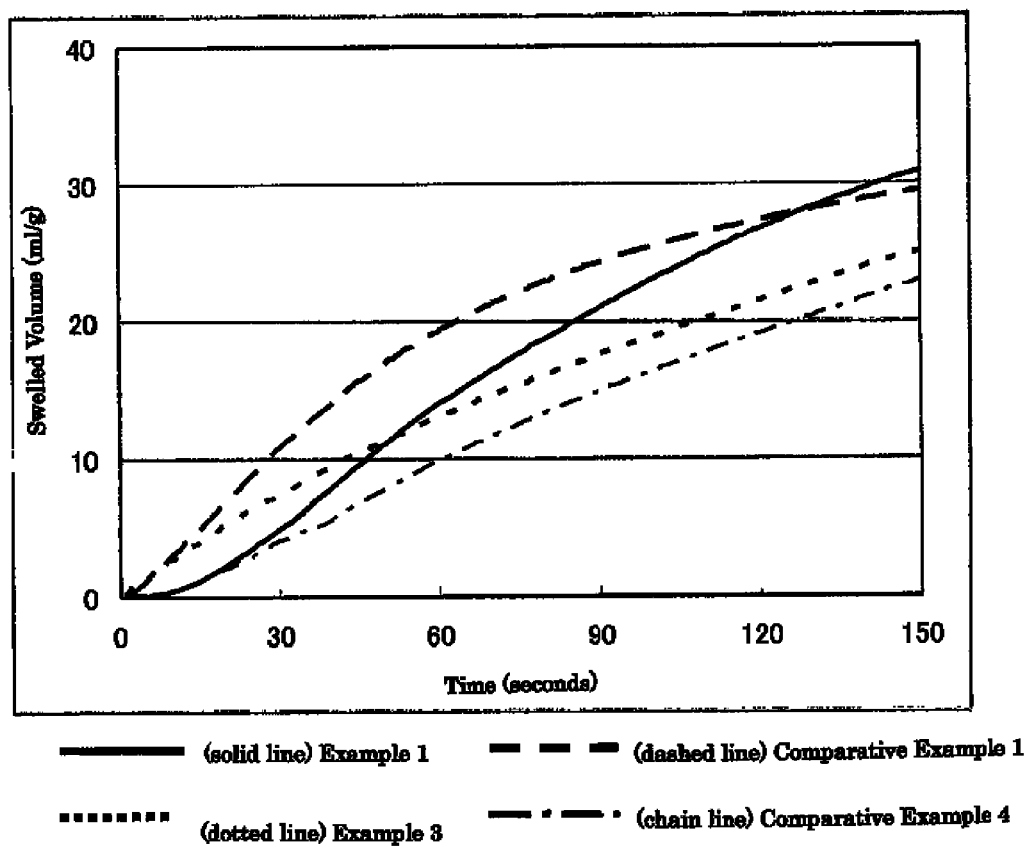
FIG. 1 shows measurement results of the absorbent resin particles obtained in Example 1 and Comparative Examples 1, 3, and 4 by a measurement method of swelled volume (until 150 seconds).

The water-soluble vinyl monomer (a1) is not particularly limited, and any of known vinyl monomers {e.g., Japanese Patent No. 3648553, JP-A-2003-165883, JP-A-2005-75982, and JP-A-2005-95759} or the like can be used.

The hydrolyzable vinyl monomer (a2) means a vinyl monomer which is converted into the water-soluble vinyl monomer (a1) by hydrolysis and is not particularly limited. Any of known vinyl monomers {e.g., Japanese Patent No. 3648553, JP-A-2003-165883, JP-A-2005-75982, and JP-A-2005-95759} or the like can be used. Herein, the water-soluble vinyl monomer means a vinyl monomer having a property that at least 100 g thereof dissolves in 100 g of water at 25 C. Also, the hydrolyzability means a property that the monomer is hydrolyzed by the action of water at 50 C and, if necessary, a catalyst (an acid, a base, or the like) to become a water-soluble one. The hydrolysis of the hydrolyzable vinyl monomer may be performed during polymerization, after polymerization, and both of them but it is preferably performed after polymerization from the viewpoint of molecular weight of the resulting absorbent resin particle and the like.

Among these, from the viewpoint of absorption characteristics and the like, the water-soluble vinyl monomer (a1) is preferable. The monomer is further preferably an anionic vinyl monomer, more preferably a vinyl monomer having a carboxy (salt) group, a sulfo (salt) group, an amino group, a carbamoyl group, an ammonio group, or a mono-, di- or tri-alkylammonio group, further preferably a vinyl monomer having a carboxy (salt) group or a carbamoyl group, particularly preferably a (meth)acrylic acid (salt) and a (meth)acrylamide, more particularly preferably a (meth)acrylic acid (salt), and most preferably an acrylic acid (salt).

Herein, the "carboxy (salt) group" means a "carboxy group" or a "carboxylate group and the "sulfonyl (salt) group" means a "sulfo group" or a "sulfonate group. Also, the (meth)acrylic acid (salt) means acrylic acid, an acrylic acid salt, methacrylic acid, or a methacrylic acid salt and the (meth)acrylamide means acrylamide or methacrylamide. Moreover, the salt includes an alkali metal (lithium, sodium, potassium, or the like) salt, an alkaline earth metal (magnesium, calcium, or the like) salt, or an ammonium ($NH_4$) salt. Among these salts, from the viewpoint of absorption characteristics and the like, the salt is preferably an alkali metal salt or an ammonium salt, further preferably an alkali metal salt, and particularly preferably a sodium salt.

In the case where either of the water-soluble vinyl monomer (a1) or the hydrolyzable vinyl monomer (a2) is used as a constituent unit, each of them may be singly used as a constituent unit or, if necessary, two or more kinds thereof may be used as constituent units. Also, the same shall apply in the case where the water-soluble vinyl monomer (a1) and the hydrolyzable vinyl monomer (a2) are used as constituent units. In the case where the water-soluble vinyl monomer (a1) and the hydrolyzable vinyl monomer (a2) are used as constituent units, the molar ratio (a1/a2) of them is preferably 75/25 to 99/1, more preferably 85/15 to 95/5, particularly preferably 90/10 to 93/7, and most preferably 91/9 to 92/8. When the ratio falls within such a range, absorption performance is further improved.

As a constituting unit of the absorbent resin particle other than the water-soluble vinyl monomer (a1) and the hydrolyzable vinyl monomer (a2), another vinyl monomer (a3) copolymerizable therewith can be used as the constituent unit.

The other vinyl monomer (a3) copolymerizable therewith is not particularly limited and any of known hydrophobic vinyl monomers {e.g., Japanese Patent No. 3648553, JP-A-2003-165883, JP-A-2005-75982, and JP-A-2005-95759} or the like can be used. The following vinyl monomers (i) to (iii) and the like can be used:

(i) aromatic ethylenic monomers having 8 to 30 carbon atoms
  styrenes such as styrene, -methylstyrene, vinyltoluene, and hydroxystyrene; vinylnaphthalene; and halogen-substituted styrenes such as dichlorostyrene;

(ii) aliphatic ethylenic monomers having 2 to 20 carbon atoms
  alkenes [ethylene, propylene, butene, isobutylene, pentene, heptene, diisobutylene, octene, dodecene, octadecene, etc.]; alkadienes [butadiene, isoprene, etc.]; and the like;

(iii) alicyclic ethylenic monomer having 5 to 15 carbon atoms
  monoethylenically unsaturated monomers [pinene, limonene, indene, etc.]; and polyethylenic vinyl polymerizable monomers [cyclopentadiene, bicyclopentadiene, ethylidenenorbornene, etc.]; and the like.

In the case where the other vinyl monomer (a3) is used as a constituent unit, the content of the other vinyl monomer (a3) unit is preferably 0.01 to 5% by mol, more preferably 0.05 to 3% by mol, further preferably 0.08 to 2% by mol, particularly preferably 0.1 to 1.5% by mol based on the mol number of the water-soluble vinyl monomer (a1) unit and the hydrolyzable vinyl monomer (a2) unit. From the viewpoint of absorption characteristics and the like, the content of the other vinyl monomer (a3) unit is most preferably 0% by mol.

The crosslinking agent (b) is not particularly limited and any of known crosslinking agents {e.g., Japanese Patent No. 3648553, JP-A-2003-165883, JP-A-2005-75982, and JP-A-2005-95759} or the like can be used.

Among these, from the viewpoint of absorption characteristics and the like, a crosslinking agent having two or more ethylenically unsaturated groups is preferable. The agent is further preferably a poly(meth)allyl ether of a polyol having 2 to 10 carbon atoms, particularly preferably triallyl cyanurate, triallyl isocyanurate, tetraallyloxyethane, or pentaerythritol triallyl ether, and most preferably pentaerythritol triallyl ether.

The content of the crosslinking agent (b) is preferably 0.001 to 5% by mol, more preferably 0.005 to 3% by mol, and particularly preferably 0.01 to 1% by mol based on the mol number of the water-soluble vinyl monomer (a1) unit and the hydrolyzable vinyl monomer (a2) unit. When the content falls within such a range, the absorption characteristics are further enhanced.

The crosslinking agent (A1) may be used singly or as a mixture of two or more kinds thereof.

The crosslinked polymer (A1) can be produced in the same manner as a conventionally known aqueous solution polymerization method {an adiabatic polymerization method, a thin-film polymerization method, a spray polymerization method, or the like; JP-A-55-133413, etc.} or a known reversed-phase suspension polymerization method {JP-B-54-30710, JP-A-56-26909, JP-A-1-5808, etc.}. Among the polymerization methods, a solution polymerization method is preferable. An aqueous solution polymerization method is particularly preferable, since organic solvent and the like are not necessarily used and hence it is advantageous in production cost.

The hydrogel {containing the crosslinked polymer and water} obtained by polymerization can be chopped as required. The size of each piece of the hydrogel after chopping (maximum diameter) is preferably 50 m to 10 cm, more preferably 100 m to 2 cm, and particularly preferably 1 mm to 1 cm. When the size falls within such a range, a drying property is further improved in the drying process.

The chopping can be carried out by a conventionally known method and the hydrogel can be chopped using a conventional chopping device {e.g., a bexmill, a rubber chopper, a pharmamill, a mincing machine, an impact crusher, or a roll crusher} or the like.

In the case where a solvent (an organic solvent, water, or the like) is used in the polymerization, the solvent is preferably removed by distillation after the polymerization. In the case where an organic solvent is contained in the solvent, the content of the organic solvent after the removal by distillation is preferably 0 to 10% by weight, more preferably 0 to 5% by weight, particularly preferable 0 to 3% by weight, and most preferably 0 to 1% by weight based on the weight of the absorbent resin particle. When the content falls within such a range, absorption performance (particularly water-retention amount) is further improved.

In the case where the solvent contains water, the water content after the removal by distillation is preferably 0 to 20% by weight, more preferably 1 to 10% by weight, particularly preferably 2 to 9% by weight, and most preferably 3 to 8% by weight based on the weight of the crosslinked polymer. When the content falls within such a range, absorption performance and the fragility of the absorbent resin particle after drying are further improved.

Herein, the content of the organic solvent and the water content can be determined by subtracting the weight of the measuring sample after heating from the weight of the same before heating, the heating being carried out by means of an infrared water content measuring machine {JE400 manufactured by KETT Co. and the like: 120 5 C, 30 minutes, atmospheric humidity before heating: 50 10% RH, lamp specification 100V, 40 W}.

As the method for removing the solvent (inclusive of water) by distillation, there may be applied a method of removal by distillation (drying) by using a hot air flow at a temperature of 80 to 230 C, a thin film drying method by means of a drum dryer that is heated at 100 to 230 C or the like, a (heating) reduced pressure drying method, a freeze drying method, a drying method using infrared ray, decantation, filtration, or the like.

The crosslinked polymer can be pulverized after drying. The pulverizing method is not particularly limited, and a conventional pulverization device {e.g., a hammer crusher, an impact crusher, a roll crusher, a jet streaming crusher} or the like can be employed. The obtained pulverized crosslinked polymer can be classified with a sieve or likes according to necessity so that the particle size is adjusted.

When the crosslinked polymer is pulverized according to necessity, the weight-average particle diameter of the crosslinked polymer (A1) is preferably 100 to 800 m, more preferably 200 to 700 m, further preferably 250 to 600 m, particularly preferably 300 to 500, and most preferably 350 to 450 m. When the weight-average particle size falls within such a range, absorption performance is further improved.

Herein, the weight-average particle diameter is measured by the method described in Perrys Chemical Engineer's Handbook 6th edition (MacGraw-Hill Book Company, 1984, page 21) using a Ro-Tap test sieve shaker and standard sieves (JIS Z8801-1:2006). That is, JIS standard sieves are superposed in an order of those of 1000 m, 850 m, 710 m, 500 m, 425 m, 355 m, 250 m, 150 m, 125 m, 75 m, and 45 m respectively and a receiving plate from the top. About 50 g of a measuring particle is placed on the top sieve and shaken for 5 minutes using a Ro-Tap test sieve shaker. The weight of the measuring particle remaining in each sieve and the receiving plate is measured, the total being regarded as 100% by weight. Then, the weight fraction of the particle on each sieve is determined. After the value is plotted on a logarithmic probability paper {the opening of the sieve (particle diameter) as abscissa and the weight fraction as ordinate}, a line connecting individual plots is drawn and a particle diameter corresponding to 50% by weight of the weight fraction is determined, the particle diameter being regarded as the weight-average particle diameter.

The smaller the content of fine particles is, the better the absorption performance is. Therefore, the content of fine particles having a particle diameter of 106 m or less (preferably 150 m or less) is preferably 3% by weight or less, more preferably 1% by weight or less based on the total weight of the particles. The content of fine particles can be determined by using the plots generated when the above-mentioned weight-average particle diameter is determined.

The apparent density of the crosslinked polymer (A1) is preferably 0.54 to 0.70 g/ml, more preferably 0.56 to 0.65 g/ml, and particularly preferably 0.58 to 0.60 g/ml. When the apparent density falls within such a range, absorption performance is further improved. The apparent density is measured at 25 C in accordance with JIS K7365:1999.

The shape of the crosslinked polymer (A1) is not particularly limited and examples thereof include an indeterminate crushed shape, a scale shape, a pearl shape, and a rice grain shape. Among these shapes, the indeterminate crushed shape is preferable from the viewpoint that the particles in such a shape can be well entangled with fibrous materials in applications such as disposable diaper and there is little possibility of the particles falling off from the fibrous materials.

The crosslinked polymer (A1) can be subjected to a surface crosslinking treatment with a surface crosslinking agent according to necessity. As the surface crosslinking agent, any of known {JP-A-59-189103, JP-A-58-180233, JP-A-61-16903, JP-A-61-211305, JP-A-61-252212, JP-A-51-136588, JP-A-61-257235, etc.} surface crosslinking agents {polyvalent glycidyls, polyvalent alcohols, polyvalent amines, polyvalent aziridines, polyvalent isocyanates, silane coupling agents, polyvalent metals, etc.} and the like can be used. Among these surface crosslinking agents, from the viewpoints of economic efficiency and absorption characteristics, the surface crosslinking agent is preferably a polyvalent glycidyl, a polyvalent alcohol, or a polyvalent amine, more preferably a polyvalent glycidyl or a polyvalent alcohol, particularly preferably a polyvalent glycidyl, and most preferably ethylene glycol diglycidyl ether.

In the case where the surface crosslinking treatment is performed, the amount (% by weight) of the surface crosslinking agent is not particularly limited since the amount can be variously varied depending on the kind of the surface crosslinking agent, conditions for crosslinking, target performance, and the like. From the viewpoint of absorption characteristics and the like, the amount is preferably 0.001 to 3% by weight, more preferably 0.005 to 2% by weight, and particularly preferably 0.01 to 1% by weight based on the weight of the water-soluble vinyl monomer (a1), the hydrolyzable vinyl monomer (a2) and the crosslinking agent (b).

In the case where the surface crosslinking treatment is performed, as the method for the surface crosslinking treatment, any of known {e.g., Japanese Patent No. 3648553, JP-A-2003-165883, JP-A-2005-75982, and JP-A-2005-95759} methods can be applied.

The absorbent resin particle of the invention preferably further comprises a hydrophobic substance (C) from the viewpoint of the above-described specific and suitable absorption rate pattern.

The hydrophobic substance (C) includes a hydrophobic substance (C1) containing a hydrocarbon group, a hydrophobic substance (C2) containing a hydrocarbon group having a fluorine atom, a hydrophobic substance (C3) having a polysiloxane structure, and the like.

Examples of the hydrophobic substance (C1) containing a hydrocarbon group include polyolefin resins, polyolefin resin derivatives, polystyrene resins, polystyrene resin derivatives, waxes, long-chain fatty acid esters, long-chain fatty acids and salts thereof, long-chain aliphatic alcohols, long-chain aliphatic amides, and mixtures of two or more thereof.

As the polyolefin resin, there may be mentioned polymers having a weight-average molecular weight of 1000 to 1000000 and containing an olefin having 2 to 4 carbon atoms {ethylene, propylene, isobutylene, isoprene, or the like} as an essential constituent monomer (the content of the olefin is at least 50% by weight based on the weight of the polyolefin resin) {e.g., polyethylene, polypropylene, polyisobutylene, poly(ethylene-isobutylene), polyisoprene, etc.}.

As the polyolefin resin derivative, there may be mentioned polymers having a weight-average molecular weight of 1000 to 1000000 and being obtained by introducing a carboxy group (—COOH), 1,3-oxo-2-oxapropylene (—COOCO—), or the like into a polyolefin resin {e.g., heat degraded polyethylene, heat degraded polypropylene, maleic acid-modified polyethylene, chlorinated polyethylene, maleic acid-modified polypropylene, ethylene-acrylic acid copolymer, ethylene-maleic anhydride copolymer, isobutylene-maleic anhydride copolymer, maleated polybutadiene, ethylene-vinyl acetate copolymer, maleated product of ethylene-vinyl acetate copolymer, etc.}.

As the polystyrene resin, a polymer having a weight-average molecular weight of 1000 to 1000000 or the like can be used.

As the polystyrene resin derivative, there may be mentioned a polymer having a weight-average molecular weight of 1000 to 1000000 and containing styrene as an essential constituent monomer (the content of the styrene is at least 50% by weight based on the weight of the polystyrene derivative) {e.g., styrene-maleic anhydride copolymer, styrene-butadiene copolymer, styrene-isobutylene copolymer, etc.}.

As the wax, there may be mentioned a wax having a melting point of 50 to 200 C {e.g., paraffin wax, beeswax, carbana wax, tallow, etc.}.

As the long-chain fatty acid ester, there may be mentioned an ester of a fatty acid having 8 to 30 carbon atoms and an alcohol having 1 to 12 carbon atoms {e.g., methyl laurate, ethyl laurate, methyl stearate, ethyl stearate, methyl oleate, ethyl oleate, glycerol monolaurate, glycerol monostearate, glycerol monooleate, pentaerythritol monolaurate, pentaerythritol monostearate, pentaerythritol monooleate, sorbitol monolaurate, sorbitol monostearate, solbitol monooleate, sucrose monopalmitate, sucrose dipalmitate, sucrose tripalmitate, sucrose monostearate, sucrose distearate, sucrose tristearate, tallow, etc.}.

As the long-chain fatty acid and the salt thereof, there may be mentioned a fatty acid having 8 to 30 carbon atoms {e.g., lauric acid, palmitic acid, stearic acid, oleic acid, dimer acid, behenic acid, etc.}. As the salt thereof, there may be mentioned a salt thereof with zinc, calcium, magnesium, or aluminum (hereinafter referred to as Zn, Ca, Mg, or Al) {e.g., Ca palmitate, Al palmitate, Ca stearate, Mg stearate, Al stearate, etc.}.

As the long-chain aliphatic alcohol, there may be mentioned an aliphatic alcohol having 8 to 30 carbon atoms {e.g., lauryl alcohol, palmityl alcohol, stearyl alcohol, oleyl alcohol, etc.}. From the viewpoint of leakage resistance of an absorbent article, palmityl alcohol, stearyl alcohol, or oleyl alcohol is preferable and stearyl alcohol is more preferable.

As the long-chain aliphatic amide, there may be mentioned an amidated product of a long-chain aliphatic primary amine having 8 to 30 carbon atoms with a carboxylic acid having a hydrocarbon group having 1 to 30 carbon atoms, an amidated product of ammonia or a primary amine having 1 to 7 carbon atoms with a long-chain fatty acid having 8 to 30 carbon atoms, an amidated product of a long-chain aliphatic secondary amine having at least one aliphatic chain having 8 to 30 carbon atoms with a carboxylic acid having 1 to 30 carbon atoms, and an amidated product of a secondary amine having two aliphatic hydrocarbon group having 1 to 7 carbon atoms with a long-chain fatty acid having 8 to 30 carbon atoms.

The amidated product of a long-chain aliphatic primary amine having 8 to 30 carbon atoms with a carboxylic acid having a hydrocarbon group having 1 to 30 carbon atoms is classified into one obtained by reacting the primary amine with the carboxylic acid in a ratio of 1:1 and one obtained by reacting the primary amine with the carboxylic acid in a ratio of 1:2. As the one obtained by reacting the primary amine with the carboxylic acid in a ratio of 1:1, there may be mentioned N-octylacetamide, N-hexacosylacetamide, N-octylheptacosanamide, N-hexacosylheptacosanamide, and the like. As the one obtained by reacting the primary amine with the carboxylic acid in a ratio of 1:2, there may be mentioned N-octyldiacetamide, N-hexacosyldiacetamide, N-octyldiheptacosanamide, N-hexacosyldiheptacosanamide, and the like. In the case of the one obtained by reacting a primary amine with a carboxylic acid in a ratio of 1:2, the carboxylic acids to be used may be the same or different.

The amidated product of ammonia or a primary amine having 1 to 7 carbon atoms with a long-chain fatty acid having 8 to 30 carbon atoms is classified into one obtained by reacting ammonia or the secondary amine with the carboxylic acid in a ratio of 1:1 and one obtained by reacting ammonia or the secondary amine with the carboxylic acid in a ratio of 1:2. As the one obtained by reacting ammonia or the secondary amine with the carboxylic acid in a ratio of 1:1, there may be mentioned nonanamide, methylnonanamide, N-heptylnonanamide, heptacosanamide, N-methylheptacosanamide, N-heptylheptacosanamide, N-hexacosylheptacosanamide, and the like. As the one obtained by reacting ammonia or the secondary amine with the carboxylic acid in a ratio of 1:2, there may be mentioned dinonanamide, N-methyldinonanamide, N-heptyldinonanamide, dioctadecanamide, N-ethyldioctadecanamide, N-heptyldioctadecanamide, diheptacosanamide, N-methyldiheptacosanamide, N-heptyldiheptacosanamide, N-hexacosyldiheptacosanamide, and the like. In the case of the one obtained by reacting ammonia or the secondary amine with the carboxylic acid in a ratio of 1:2, the carboxylic acids to be used may be the same or different.

As the amidated product of a long-chain aliphatic secondary amine having at least one aliphatic chain having 8 to 30 carbon atoms with a carboxylic acid having to 30 carbon atoms, there may be mentioned N-methyloctylacetamide, N-methylhexacosylacetamide, N-octylhexacosylacetamide, N-dihexacosylacetamide, N-methyloctylheptacosanamide, N-methylhexacosylheptacosanamide, N-octylhexacosylheptacosanamide, N-dihexacosylheptacosanamide, and the like.

As the amidated product of a secondary amine having two aliphatic hydrocarbon groups having 1 to 7 carbon atoms with a long-chain fatty acid having 8 to 30 carbon atoms, there may be mentioned N-dimethylnonanamide, N-methylheptylnonanamide, N-diheptylnonanamide, N-dimethylheptacosanamide, N-methylheptylheptacosanamide, N-diheptylheptacosanamide, and the like.

Examples of the hydrophobic substance (C2) containing a hydrocarbon group having a fluorine atom include perfluoroalkanes, perfluoroalkenes, perfluoroaryls, perfluoroalkyl ethers, perfluoroalkyl carboxylic acids, perfluoroalkyl alcohols, and mixtures of two or more thereof.

As the perfluoroalkane, there may be mentioned an alkane having 4 to 42 fluorine atoms and 1 to 20 carbon atoms {e.g., trifluoromethane, pentafluoroethane, pentafluoropropane, heptafluoropropane, heptafluorobutane, nonafluorohexane, tridecafluorooctane, heptadecafluorododecane, etc.}.

As the perfluoroalkene, there may be mentioned an alkene having 4 to 42 fluorine atoms and 2 to 20 carbon atoms {e.g., trifluoroethylene, pentafluoropropene, trifluoropropene, heptafluorobutene, nonafluorohexene, tridecafluorooctene, heptadecafluorododecene, etc.}.

As the perfluoroaryl, there may be mentioned an aryl compound having 4 to 42 fluorine atoms and 6 to 20 carbon atoms {e.g., trifluorobenzene, pentafluorotoluene, trifluoronaphthalene, heptafluorobenzene, nonafluoroxylene, tridecafluorooctylbenzene, heptadecafluorododecylbenzene, etc.}.

As the perfluoroalkyl ether, there may be mentioned an ether having 2 to 82 fluorine atoms and 2 to carbon atoms {e.g., ditrifluoromethyl ether, dipentafluoroethyl ether, dipentafluoropropyl ether, diheptafluoropropyl ether, diheptafluorobutyl ether, dinonafluorohexyl ether, ditridecafluorooctyl ether, diheptadecafluorododecyl ether, etc.}.

As the perfluoroalkylcarboxylic acid, there may be mentioned a carboxylic acid having 3 to 41 fluorine atoms and 1 to 21 carbon atoms {e.g., pentafluoroethanoic acid, pentafluoropropanoic acid, heptafluoropropanoic acid, heptafluorobutanoic acid, nonafluorohexanoic acid, tridecafluorooctanoic acid, heptadecafluorododecanoic acid, and metal (alkali metal, alkaline earth metal, etc.) salts thereof, etc.}.

As the perfluoroalkyl alcohol, there may be mentioned an alcohol having 3 to 41 fluorine atoms and 1 to 20 carbon atoms {e.g., pentafluoroethanol, pentafluoropropanol, heptafluoropropanol, heptafluorobutanol, nonafluorohexanol, tridecafluorooctanol, heptadecafluorododecanol, etc.} and an ethylene oxide adduct of the alcohol (1 to 20 mol of ethylene oxide per mol of the alcohol).

As the mixture of two or more thereof, there may be mentioned a mixture of the perfluoroalkylcarboxylic acid and the perfluoroalkyl alcohol {e.g., a mixture of pentafluoroethanoic acid and pentafluoroethanol, etc.}.

Examples of the hydrophobic substance (C3) having a polysiloxane structure include polydimethylsiloxane, polyether-modified polysiloxane {polyoxyethylene-modified polysiloxane, poly(oxyethylene/oxypropylene)-modified polysiloxane, etc.}, carboxy-modified polysiloxane, epoxy-modified polysiloxane, amino-modified polysiloxane, alkoxy-modified polysiloxane, mixtures thereof, and the like.

The position of an organic group (modifying group) of the modified silicones {polyether-modified polysiloxane, carboxy-modified polysiloxane, epoxy-modified polysiloxane, amino-modified polysiloxane, etc.} is not particularly limited, and it may be a side chain of the polysiloxane, both terminals of the polysiloxane, one terminal of the polysiloxane, or both of a side chain and both terminals of the polysiloxane. Among these, from the viewpoint of absorption characteristics and the like, the position is preferably either a side chain of the polysiloxane or both of a side chain and both terminals of the polysiloxane and more preferably both of a side chain and both terminals of the polysiloxane.

Examples of the organic group (modifying group) of the polyether-modified polysiloxane include groups containing a polyoxyethylene group or a poly(oxyethylene-oxypropylene) group, and the like. The content (number) of the oxyethylene group and/or oxypropylene group contained in the polyether-modified polysiloxyane is preferably 2 to 40, more preferably 5 to 30, particularly preferably 7 to 20, and most preferably 10 to 15 per one polyether-modified polysiloxane molecule. When the content falls within such a range, absorption characteristics are further improved. Also, in the case where an oxyethylene group and an oxypropylene group are contained, the content of the oxyethylene group is preferably 1 to 30% by weight, more preferably 3 to 25% by weight, and particularly preferably 5 to 20% by weight based on the weight of the polysiloxane. When the content falls within such a range, absorption characteristics are further improved.

The polyether-modified polysiloxane is commercially easily available and, for example, the following commercial products {modification position, kind of oxyalkylene} can be preferably exemplified.

*Products manufactured by Shin-Etsu Chemical Co., Ltd.
KF-945 {side chain, oxyethylene and oxypropylene}, KF-6020 {side chain, oxyethylene and oxypropylene}, X-22-6191 {side chain, oxyethylene and oxypropylene}, X-22-4952 {side chain, oxyethylene and oxypropylene}, X-22-4272 {side chain, oxyethylene and oxypropylene}, X-22-6266 {side chain, oxyethylene and oxypropylene}.

*Products manufactured by Dow Corning Toray Co., Ltd.
FZ-2110 {both terminals, oxyethylene and oxypropylene}, FZ-2122 {both terminals, oxyethylene and oxypropylene}, FZ-7006 {both terminals, oxyethylene and oxypropylene}, FZ-2166 {both terminals, oxyethylene and oxypropylene}, FZ-2164 {both terminals, oxyethylene and oxypropylene}, FZ-2154 {both terminals, oxyethylene and oxypropylene}, FZ-2203 {both terminals, oxyethylene and oxypropylene}, and FZ-2207 {both terminals, oxyethylene and oxypropylene}.

Examples of the organic group (modifying group) of the carboxy-modified polysiloxane include groups containing a carboxy group and the like. Examples of the organic group (modifying group) of the epoxy-modified polysiloxane include groups containing an epoxy group and the like. Examples of the organic group (modifying group) of the amino-modified polysiloxane include groups containing an amino group (primary, secondary, or tertiary amino group) and the like. The content of the organic group (modifying group) in such a modified silicone is preferably 200 to 11000 g/mol, more preferably 600 to 8000 g/mol, and particularly preferably 1000 to 4000 g/mol, as a carboxy equivalent, an epoxy equivalent, or an amino equivalent. When the content falls within such a range, absorption characteristics are further improved. Herein, the carboxy equivalent is measured in accordance with "16. Total Acid Value Test" of JIS C2101: 1999. Moreover, the epoxy equivalent is determined in accordance with JIS K7236:2001. Also, the amino equivalent is measured in accordance with "8. Potentiometric Titration (base value-hydrochloric acid method)" of JIS K2501:2003.

The carboxy-modified polysiloxane is commercially easily available and, for example, the following commercial products {modification position, carboxy equivalent (g/mol)} can be preferably exemplified.
*Products manufactured by Shin-Etsu Chemical Co., Ltd.
X-22-3701E {side chain, 4000}, X-22-162C {both terminals, 2300}, X-22-3710 {one terminal, 1450}.
*Products manufactured by Dow Corning Toray Co., Ltd.
BY 16-880 {side chain, 3500}, BY 16-750 {both terminals, 750}, BY 16-840 {side chain, 3500}, SF8418 {side chain, 3500}.

The epoxy-modified polysiloxane is commercially easily available and, for example, the following commercial products {modification position, epoxy equivalent} can be preferably exemplified.
*Products manufactured by Shin-Etsu Chemical Co., Ltd.
X-22-343 {side chain, 525}, KF-101 {side chain, 350}, KF-1001 {side chain, 3500}, X-22-2000 {side chain, 620}, X-22-2046 {side chain, 600}, KF-102 {side chain, 3600}, X-22-4741 {side chain, 2500}, KF-1002 {side chain, 4300}, X-22-3000T {side chain, 250}, X-22-163 {both terminals, 200}, KF-105 {both terminals, 490}, X-22-163A {both terminals, 1000}, X-22-163B {both terminals, 1750}, X-22-163C {both terminals, 2700}, X-22-169AS {both terminals, 500}, X-22-169B {both terminals, 1700}, X-22-173DX {one terminal, 4500}, X-22-9002 {side chain/both terminals, 5000}.
*Products manufactured by Dow Corning Toray Co., Ltd.
FZ-3720 {side chain, 1200}, BY 16-839 {side chain, 3700}, SF 8411 {side chain, 3200}, SF 8413 {side chain, 3800}, SF 8421 {side chain, 11000}, BY 16-876 {side chain, 2800}, FZ-3736 {side chain, 5000}, BY 16-855D {side chain, 180}, BY 16-8 {side chain, 3700}.

The amino-modified polysiloxane is commercially easily available and, for example, the following commercial products {modification position, amino equivalent} can be preferably exemplified.
*Products manufactured by Shin-Etsu Chemical Co., Ltd.
KF-865 {side chain, 5000}, KF-864 {side chain, 3800}, KF-859 {side chain, 6000}, KF-393 {side chain, 350}, KF-860 {side chain, 7600}, KF-880 {side chain, 1800}, KF-8004 {side chain, 1500}, KF-8002 {side chain, 1700}, KF-8005 {side chain, 11000}, KF-867 {side chain, 1700}, X-22-3820W {side chain, 55000}, KF-869 {side chain, 8800}, KF-861 {side chain, 2000}, X-22-3939A {side chain, 1500}, KF-877 {side chain, 5200}, PAM-E {both terminals, 130}, KF-8010 {both terminals, 430}, X-22-161A {both terminals, 800}, X-22-161B {both terminals, 1500}, KF-8012 {both terminals, 2200}, KF-8008 {both terminals, 5700}, X-22-1660B-3 {both terminals, 2200}, KF-857 {side chain, 2200}, KF-8001 {side chain, 1900}, KF-862 {side chain, 1900}, X-22-9192 {side chain, 6500}.
*Products manufactured by Dow Corning Toray Co., Ltd.
FZ-3707 {side chain, 1500}, FZ-3504 {side chain, 1000}, BY 16-205 {side chain, 4000}, FZ-3760 {side chain, 1500}, FZ-3705 {side chain, 4000}, BY 16-209 {side chain, 1800}, FZ-3710 {side chain, 1800}, SF 8417 {side chain, 1800}, BY 16-849 {side chain, 600}, BY 16-850 {side chain, 3300}, BY 16-879B {side chain, 8000}, BY 16-892 {side chain, 2000}, FZ-3501 {side chain, 3000}, FZ-3785 {side chain, 6000}, BY 16-872 {side chain, 1800}, BY 16-213 {side chain, 2700}, BY 16-203 {side chain, 1900}, BY 16-898 {side chain, 2900}, BY 16-890 {side chain, 1900}, BY 16-893 {side chain, 4000}, FZ-3789 {side chain, 1900}, BY 16-871 {both terminals, 130}, BY 16-853C {both terminals, 360}, BY 16-853U {both terminals, 450}.

As a mixture thereof, there may be mentioned a mixture of polydimethylsiloxane and a carboxyl-modified polysiloxane, a mixture of a polyether-modified polysiloxane and an amino-modified polysiloxane, or the like.

The viscosity (mPa·s, 25 C) of the hydrophobic substance having a polysiloxane structure is preferably 10 to 5000 mPa·s, more preferably 15 to 3000 mPa·s, and particularly preferably 20 to 1500 mPa·s. When the viscosity falls within such a range, absorption characteristics are further improved. Herein, the viscosity is measured in accordance with JIS Z8803-1991 "Viscosity of Liquid" 9. the viscosimetry by means of a circular cone and circular cone-flat plate type rotary viscometer {for example, the viscosity is measured by means of an E type viscometer (RE80L manufactured by Toki Sangyo Co., Ltd., a circular cone having a diameter of 7 mm and an angle of 5.24 $10^{-2}$ rad}.

The HLB value of the hydrophobic substance (C) is preferably 1 to 10, more preferably 2 to 8, and particularly preferably 3 to 7. When the HLB value falls within such a range, the leakage resistance of an absorbent article is further improved. The HLB value means a hydrophilicity-hydrophobicity balance (HLB) value and is determined by the Oda method (Shin-Kaimen Kassei Zai Nyumon, page 197, Takehiko Fujimoto, published by Sanyo Chemical Industries Ltd., 1981).

From the viewpoint of the leakage resistance of an absorbent article, the hydrophobic substance (C) is preferably a hydrophobic substance (C1) containing a hydrocarbon group, more preferably a long-chain fatty acid ester, a long-chain fatty acid and a salt thereof, a long-chain aliphatic alcohol, and a long-chain aliphatic amide, further preferably sorbitol stearate, sucrose stearate, stearic acid, Mg stearate, Ca stearate, Zn stearate, and Al stearate, particularly preferably sucrose stearate and Mg stearate, and most preferably sucrose monostearate.

The hydrophobic substance (C) may be present at any portion of the absorbent resin particle.

From the viewpoints of skin irritation resistance of an absorbent article and leakage resistance of an absorbent article, the content of the hydrophobic substance (C) in the inside of the absorbent resin particle is usually 0.01 to 10.0% by weight, preferably 0.01 to 5.0% by weight, more preferably 0.05 to 2.0% by weight, and particularly preferably 0.1 to 1.0% by weight based on the weight of the crosslinked polymer (A1).

From the viewpoints of skin irritation resistance of an absorbent article and leakage resistance of an absorbent article, the content of the hydrophobic substance (C) present on the surface of the absorbent resin particle is usually 0.001 to 1.0% by weight, preferably 0.005 to 0.5% by weight, more preferably 0.01 to 0.3% by weight, and particularly preferably 0.01 to 0.1% by weight based on the weight of the crosslinked polymer (A1).

Incidentally, the content of the hydrophobic substance present on the surface is measured by the following method. The content of the hydrophobic substance present in the inside is obtained by subtracting the content of the hydrophobic substance on the surface from the total added amount of the hydrophobic substance.

<Measuring Method of Content of Hydrophobic Substance (C) on Surface>

To a glass-made eggplant-shape flask fitted with a cooling tube are added 100 parts by weight of an absorbent resin particle and 300 parts by weight of an organic solvent (an organic solvent capable of dissolution of at least 0.01 part by weight of the hydrophobic substance (C) in 100 parts by weight of the organic solvent at 25 to 110 C. A temperature capable of dissolution is regarded as dissolution temperature) and the whole is allowed to stand at the dissolution temperature for 24 hours, thereby an extraction solution of the hydrophobic substance being obtained. After the extraction solution is filtrated using a filter paper and is collected into a glass-made eggplant-shape flask weighed beforehand, the solvent is evaporated on a rotary evaporator and then the flask is weighed. An amount of the extracted evaporation residue is determined by subtracting the weight of the eggplant-shape flask weighed beforehand from the weight after the evaporation of the filtration solution.

Using the sample remaining on the filter paper after extraction, the same operation is repeated twice and the total amount of the evaporation residue obtained by three-time extraction is regarded as the content (% by weight) of the hydrophobic substance (C) on the surface.

With regard to the structure wherein the hydrophobic substance (C) is present in the inside of the absorbent resin particle and a part thereof is present on the surface, the absorbent resin particle can be produced by (1) a method of mixing and/or kneading the hydrophobic substance (C) and a hydrogel of the crosslinked polymer (A1) or (2) a method of obtaining a hydrogel of the crosslinked polymer (A1) by polymerizing constituent units in the presence of the hydrophobic substance (C).

In the method (1), as a shape of the hydrophobic substance (C), one processed into a pulverized form, a bead form, a rod form, or a fibrous form can be used. From the viewpoint of leakage resistance of an absorbent article, a pulverized form or a bead form is preferable, and a bead form is more preferable. The volume-average particle diameter of the hydrophobic substance (C) is preferably 0.5 to 100 m, more preferably 1 to 30 m, and particularly preferably 2 to 20 m.

The method for mixing the crosslinked polymer (A1) and the hydrophobic substance (C) is not particularly limited as long as they are mixed so that the hydrophobic substance (C) is present in the inside of the crosslinked polymer (A1).

However, the hydrophobic substance (C) is preferably mixed, not with a dried-form crosslinked polymer (A1), but with a hydrogel of the crosslinked polymer (A1) or a polymerization solution of the crosslinked polymer (A1), and is more preferably mixed with a hydrogel of the crosslinked polymer (A1). In the mixing operation, they are preferably mixed homogeneously in a kneading-like manner.

When the crosslinked polymer (A1) is obtained by the aqueous solution polymerization method, the timing of mixing and/or kneading the hydrophobic substance (C) with the crosslinked polymer (A1) is not particularly limited, and the timing may be either during the polymerization process {the crosslinked polymer (A1) is produced in the presence of the hydrophobic substance (C)}, immediately after the polymerization process, during the process of crushing (mincing) the hydrogel, during the process of drying the hydrogel, or the like. Among these, from the viewpoints of leakage resistance and the like of an absorbent article, the timing is preferably immediately after the polymerization process or during the process of crushing (mincing) the hydrogel, and more preferably during the process of crushing (mincing) the hydrogel. Moreover, in the case where the hydrophobic substance (C) is a long-chain fatty acid salt, a long-chain fatty acid salt itself is used but a long-chain fatty acid and a metal hydroxide may be mixed and charged at the addition process or they may be charged separately.

When the crosslinked polymer (A1) is obtained by the reverse-phase suspension polymerization method or the emulsion polymerization method, the timing of mixing the hydrophobic substance (C) with the crosslinked polymer (A1) is not particularly limited, and the timing may be either during a polymerization process {the crosslinked polymer (A) is produced in the presence of the hydrophobic substance (C)}, immediately after the polymerization process, during the dehydration process (during a dehydration process until moisture becomes approximately 10% by weight), immediately after the dehydration process, during the process of separating and removing by distillation an organic solvent used for polymerization, during the process of drying the hydrogel, or the like. Among these, from the viewpoints of leakage resistance and the like of an absorbent article, the timing is preferably during the polymerization process, immediately after the polymerization process, during the dehydration process, immediately after the dehydration process, or during the process for separating and removing by distillation an organic solvent used for polymerization, and further preferably, during the polymerization process or immediately after the polymerization process.

In the case where the mixing is carried out during the process of crushing or drying the hydrogel, a conventional device can be used, such as a bexmill, a rubber chopper, a pharmamill, a mincing machine, an impact crusher, or a roll crusher as a mixing device. In the case where the mixing is carried out in a polymerization solution, a device with a relatively high stirring power such as a homomixer or a biomixer can be used. Alternatively, in the case where the mixing is carried out during the process of drying the hydrogel, a kneading device such as an SV mixer may be used.

The mixing temperature (C) can be appropriately controlled by the process of adding the hydrophobic substance (C). For example, the mixing temperature in the case of adding and mixing immediately after the polymerization process and during crushing (mincing) the hydrogel is preferably 20 to 100 C, more preferably 40 to 90 C, and particularly 50 to 80 C. When the mixing temperature falls within such a range, homogeneous mixing can be further facilitated and the absorption characteristics are further improved.

In the method (2) in which the crosslinked polymer (A1) is produced in the presence of the hydrophobic substance (C), the hydrophobic substance (C) is preferably dissolved or emulsified (dispersed) in the polymerization solution of the crosslinked polymer (A). In the case where it is difficult to make the hydrophobic substance (C) homogeneous, the substance can be made homogeneous during the process of crushing the hydrogel. The method can be carried out while the hydrophobic substance (C) is deposited with the progress of the polymerization of the crosslinked polymer (A1). Other than the fact that polymerization is carried out in the presence of the hydrophobic substance (C), the polymerization method is the same as the case of the crosslinked polymer (A1).

The hydrophobic substance (C) may be used in a state of being dissolved and/or emulsified in water and/or a volatile solvent (however, no emulsifier is used). The volatile solvent is, from the viewpoint of removability, preferably a volatile solvent that exhibits a vapor pressure at 20 C of 0.13 to 5.3 Pa, more preferably 0.15 to 4.5 Pa, and particularly preferably 0.23 to 3.8 Pa.

Examples of the volatile solvent include alcohols having 1 to 3 carbon atoms (methanol, ethanol, isopropyl alcohol, etc.), hydrocarbons having 5 to 8 carbon atoms (pentane, hexane, cyclohexane, toluene, etc.), ethers having 2 to 4 carbon atoms (dimethyl ether, diethyl ether, tetrahydrofuran, etc.), ketones having 3 to 4 carbon atoms (acetone, methyl ethyl ketone, etc.), and esters having 3 to 5 carbon atoms (ethyl formate, ethyl acetate, isopropyl acetate, diethyl carbonate, etc.). In the case where water and/or a volatile solvent are used, the amount of the same used is preferably 1 to 900% by weight, more preferably 5 to 700% by weight, and particularly preferably 10 to 400% by weight based on the weight of the hydrophobic substance (C). In the case where water and a volatile solvent are used, the amount of water used is preferably 50 to 98% by weight, more preferably 60 to 95% by weight, and particularly preferably 70 to 90% by weight based on the weight of water and the volatile solvent.

The hydrogel containing the hydrophobic substance (C) can be chopped as required. The size of each piece of the hydrogel after chopping (maximum diameter) is preferably 50 m to 10 cm, more preferably 100 m to 2 cm, and particularly preferably 1 mm to 1 cm. When the size falls within such a range, a drying property is further improved in the drying process.

As a chopping method, the same method as the case of the crosslinked polymer (A1) can be adopted.

In the case where a solvent (inclusive of an organic solvent and/or water) is used in the production of the absorbent resin particle, the solvent can be removed by distillation after the polymerization.

In the case where an organic solvent is contained in the solvent, the content of the organic solvent after the removal by distillation is preferably 0 to 10% by weight, more preferably 0 to 5% by weight, particularly preferable 0 to 3% by weight, and most preferably 0 to 1% by weight based on the weight of the absorbent resin particle. When the content falls within such a range, absorption performance (particularly water-retention amount) of the absorbent resin particle is further improved.

Also, in the case where the solvent contains water, the water content after the removal by distillation is preferably 0 to 20% by weight, more preferably 1 to 10% by weight, particularly preferably 2 to 9% by weight, and most preferably 3 to 8% by weight based on the weight of the absorbent resin particle. When the content falls within such a range, absorption performance (particularly water-retention amount) and the fragility of the absorbent resin particle after drying are further improved.

Herein, the method of measuring the content of the organic solvent and the water content and the method of removing the solvent by distillation are the same as the case of the crosslinked polymer (A1).

The absorbent resin particle can be pulverized. In the case where the absorbent resin particle contains a solvent, the particle is preferably pulverized after the solvent is removed by distillation (dried).

In the case where pulverization is performed, a weight-average particle diameter after pulverization is preferably 100 to 800 m, more preferably 200 to 700 m, further preferably 250 to 600 mm, particularly preferably 300 to 500 m, and most preferably 350 to 450 m. When the weight-average particle diameter falls within such a range, handling ability (powder flowability and the like of the absorbent resin particle) after pulverization and the skin irritation resistance of an absorbent article are further improved. Also, the weight-average particle diameter can be measured in the same manner as in the case of the crosslinked polymer (A1).

The smaller the content of fine particles is, the better the absorption performance is. Therefore, preferably, the content of fine particles having a particle diameter of 106 m or less is 3% by weight or less based on the total weight of the particles. More preferably, the content of fine particles having a particle diameter of 150 m or less is 3% by weight or less based on the total weight of the particles. The content of the fine particles can be determined by using plots generated when the above-described weight-average particle diameter is determined.

For the pulverization and particle size control, the same method as in the case of the crosslinked polymer (A1) can be adopted.

The apparent density of the absorbent resin particle of the invention is preferably 0.54 to 0.70 g/ml, more preferably 0.56 to 0.65 g/ml, and particularly preferably 0.58 to 0.60 g/ml. When the apparent density falls within such a range, the skin irritation resistance of an absorbent article is further improved. The apparent density can be measured as in the case of the crosslinked polymer (A1).

The shape of the absorbent resin particle is not particularly limited and examples thereof include an indeterminate crushed shape, a scale shape, a pearl shape, and a rice grain shape. Among these shapes, the indeterminate crushed shape is preferable from the viewpoint that the particles in such a shape can be well entangled with fibrous materials in applications such as a disposable diaper and there is little possibility of the particles falling off from the fibrous materials.

The absorbent resin particle can be subjected to a surface crosslinking treatment according to necessity. As the crosslinking agent for the surface crosslinking (surface crosslinking agent), the same ones as the internal crosslinking agent (b) can be used. As the surface crosslinking agent, from the viewpoints of absorption performance and the like of the absorbent resin particle, the surface crosslinking agent is preferably a crosslinking agent (b3) having at least two functional groups reactive with a water-soluble substituent of the water-soluble vinyl monomer (a1) and/or a water-soluble substituent formed by hydrolysis of the vinyl monomer (a2), more preferably a polyvalent glycidyl, particularly preferably ethylene glycol diglycidyl ether or glycerin diglycidyl ether, and most preferably ethylene glycol diglycidyl ether.

In the case where the surface crosslinking is performed, the content of the surface crosslinking agent is preferably 0.001 to 7% by weight, more preferably 0.002 to 5% by weight, and particularly preferably 0.003 to 4% by weight based on the total weight of the vinyl monomer (a1) and/or (a2), the internal crosslinking agent (b), and the other vinyl monomer (a3) used according to necessity. That is, in this case, the upper limit of the content of the surface crosslinking agent is preferably 7, more preferably 5, and particularly preferably 4 based on the total weight of (a1) and/or (a2), (b) and (a3).

Similarly, the lower limit is preferably 0.001% by weight, more preferably 0.002% by weight, and particularly preferably 0.003% by weight. When the content falls within such a range, the absorption performance is further improved. The surface crosslinking can be achieved by a method of spraying or impregnating the absorbent resin particle with an aqueous solution containing the surface crosslinking agent and subsequently subjecting the particle to a heat treatment (100 to 200 C).

The absorbent resin particle of the invention can be further coated with an inorganic powder (D) on the surface. Examples of the inorganic powder (D) include a hydrophilic inorganic particle (d1), a hydrophobic inorganic particle (d2), and the like.

Examples of the hydrophilic inorganic substance (d1) include particles of glass, silica gel, silica, and clay.

Examples of the hydrophobic inorganic substance (d2) include particles of carbon fiber, kaolin, talc, mica, bentonite, sericite, asbestos, and Shirasu (volcanic ash) or likes.

Among these, the hydrophilic inorganic particle (d1) is preferable, and silica is most preferable.

Regarding the shape of the hydrophilic inorganic particle (d1) and the hydrophobic inorganic particle (d2), the shape may be any one of an indeterminate shape (crushed shape), a spherical shape, a film shape, a rod shape, a fibrous shape, and the like, among which the indeterminate shape (crushed shape) or the spherical shape is preferable and the spherical shape is more preferable.

The content of the inorganic powder (D) is preferably 0.01 to 3.0% by weight, more preferably 0.05 to 1.0% by weight, further preferably 0.1 to 0.8% by weight, particularly preferably 0.2 to 0.7% by weight, and most preferably 0.3 to 0.6% by weight based on the weight of the crosslinked polymer (A1). When the content falls within such a range, the skin irritation resistance of an absorbent article is further improved.

The absorbent resin particle of the invention may further contain other additives {e.g., known (JP-A-2003-225565, JP-A-2006-131767, etc.) antiseptic agents, fungicides, antibacterial agents, antioxidants, ultraviolet absorbers, coloring agents, perfuming agents, deodorizers, organic fibrous materials, and the like}. In the case where the absorbent resin particle contains such additives, the content of the additives is preferably 0.001 to 10% by weight, more preferably 0.01 to 5% by weight, particularly preferably 0.05 to 1% by weight, and most preferably 0.1 to 0.5% by weight based on the weight of the crosslinked polymer (A1).

In the measurement method of swelled volume per 1 g of the absorbent resin particle of the invention against physiological saline, the ratio (t2/t1) of the time (t2) until the swelled volume reaches 40 ml to the time (t1) until the swelled volume reaches 5 ml is 5 to 20, preferably 5 to 15, and most preferably 5 to 10. Moreover, the t1 is preferably 20 to 60 seconds, more preferably 20 to 50 seconds, and most preferably 30 to 40 seconds.

When the ratio and the time fall within such ranges, the skin irritation resistance of an absorbent article is further improved. By controlling the content of the hydrophobic substance (C) to the above-described preferable ranges, the time until the swelled volume reaches a specific volume determined by the measurement method of swelled volume can be controlled to a preferable range. Furthermore, by controlling the apparent density of the absorbent resin particle, the weight-average particle diameter of the absorbent resin particle, and the like to the above-described preferable ranges, the time until the swelled volume reaches a specific volume can be controlled to a more preferable range.

Figure 3:
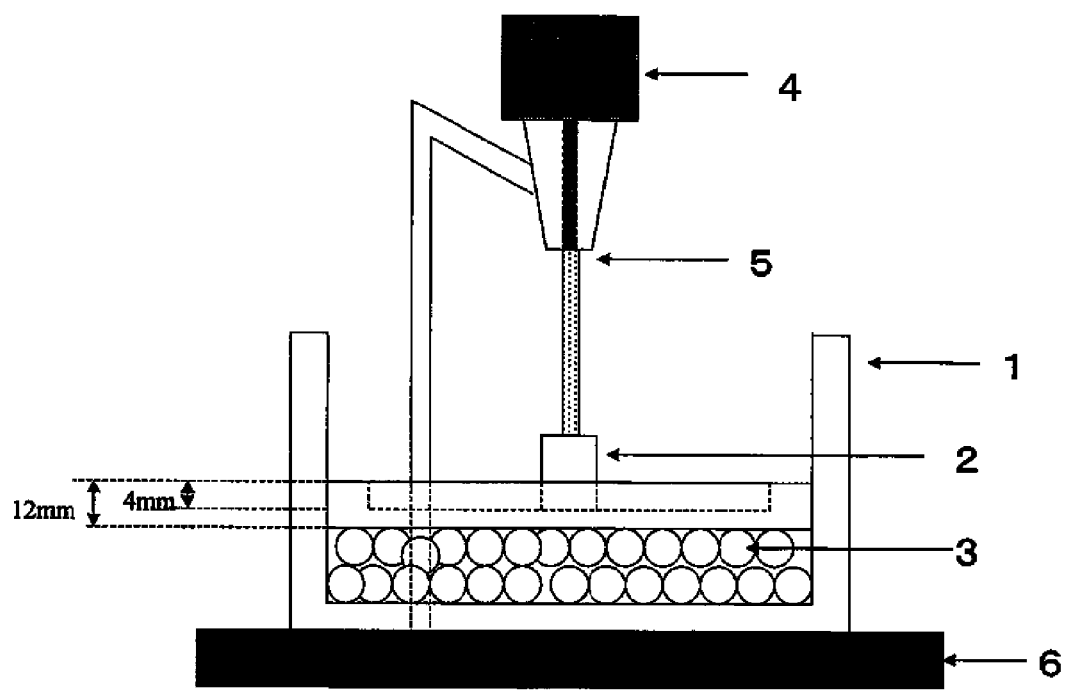
FIG. 3 is a front cross-sectional view schematically illustrating a whole device for measuring swelled volume by a measurement method of swelled volume.
Figure 4:
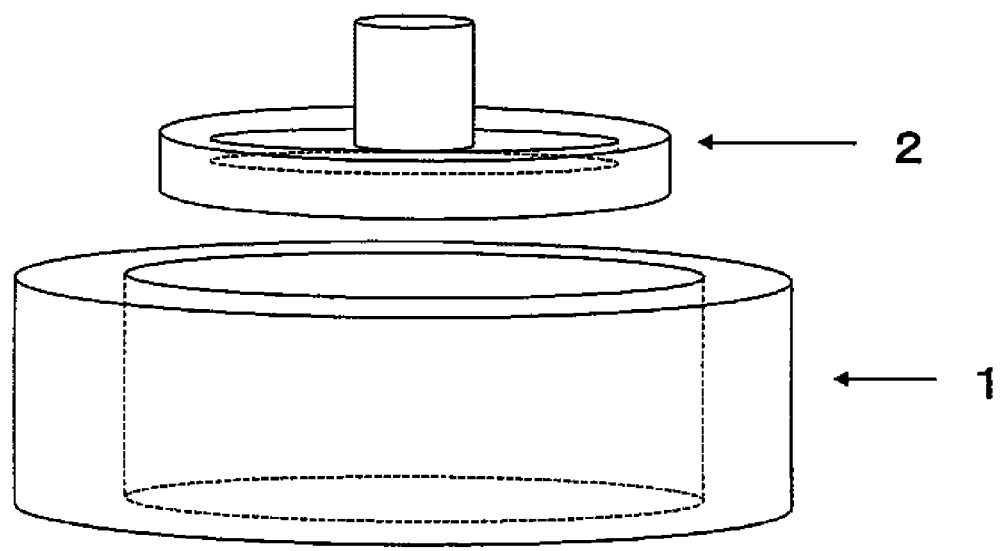
FIG. 4 is a lateral projection view schematically illustrating a cylinder 1 with a bottom plate and a disk 2 with a handgrip for measuring swelled volume by a measurement method of swelled volume.

The measurement method of swelled volume is a measuring method in a room at 25 2 C and at a humidity of 50 10% using a device shown in FIG. 3. In this connection, the temperature of the physiological saline to be used is controlled to 25 2 C beforehand.

<Device for Measurement of Swelled Volume>

The device shown in FIG. 3 is composed of an acryl-made cylinder 1 with a bottom plate and an acryl-made disk 2 with a handgrip.

The cylinder 1 with a bottom plate is a cylinder with a bottom plate wherein a bottom plate having a thickness of 5 mm is attached to one side of a cylinder having an inner diameter of 81 mm and a length of 35 mm and the remaining side is opened.

The acryl-made disk 2 is a disk having an outer diameter of 80.5 mm and a thickness of 12 mm. The disk 2 has a circular concave having a diameter of 70.5 mm and a depth of 4 mm at a position where the center of the disk is coincident with the center of the circle. Also, the disk 2 has a column having a length of 13 mm and an outer diameter of 15 mm on the circular concave portion as a handgrip at a position where the center of the disk 2 is coincident with the center of bottom face of the column.

Figure 5:
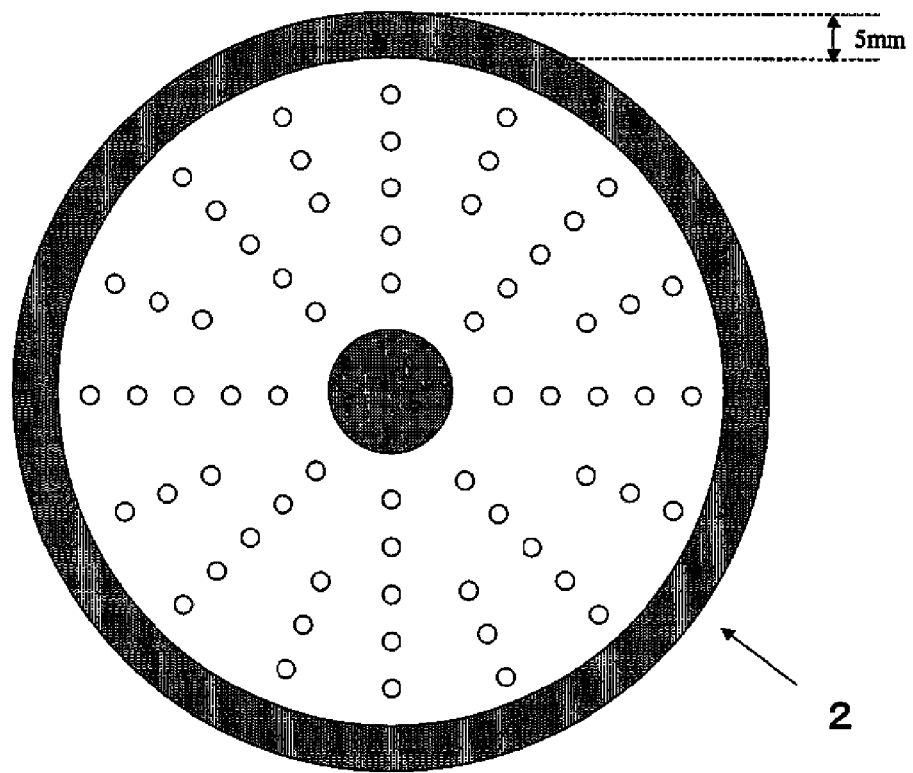
FIG. 5 is a top view schematically illustrating a disk 2 with a handgrip for measuring swelled volume by a measurement method of swelled volume.

Furthermore, the disk 2 has 64 holes having a diameter of 2 mm in a radial pattern (see FIG. 5). The following will describe the holes of the disk 2. The holes are made such a manner that 5 holes having a diameter of 2 mm are present on each of lines that divide the disk equal eight portions and at equal intervals of 5 mm between a position of 10 mm from the center of the disk and a position of 30 mm therefrom (40 holes in total). Additionally, 3 holes having a diameter of 2 mm are present on each of lines that divide the disk equal eight portions and at equal intervals of 5 mm between a position of 20 mm from the center of the disk and a position of 30 mm therefrom, the lines being tilted at 22.5 from the above-described equally dividing lines (24 holes in total).

The weight of the disk 2 with the handgrip is 60 5 g.

<Measuring Method of Swelled Volume>

Into the cylinder 1 with the bottom plate positioned perpendicularly, 2.50 g of a measuring sample sieved to have a particle diameter ranging 150 to 850 m is weighed and charged so that the sample is placed in an almost uniform thickness on the bottom of the cylinder 1 with the bottom plate. The disk 2 is placed thereon so that the handgrip comes up and the distance from the bottom face of the cylinder to the top face of the handgrip of the disk is measured using a thickness meter (e.g., a digimatic indicator ID-F150 manufactured by Mitutoyo Co.). On this occasion, the pressure imparted to the absorbent resin particle by the weight of the measuring rod of the digimatic indicator (140 10 g) and the weight of the disk 2 with the handgrip is 3.9 0.3 g/cm$^2$. Then, the display of thickness indicated by the digimatic indicator is made zero. Subsequently, 120 ml of physiological saline is charged into the cylinder 1 with the bottom plate within 2 seconds.

The time of the start of charging is regarded as zero and the distance H (cm) of elevation of the disk 2 with the passage of time from the start of charging is recorded as continuous data. By calculating the swelled volume (ml) per 1 g of the absorbent resin particle according to the following equation, data of change in swelled volume against time are obtained. From the data, the time (t1) until the swelled volume reaches 5 ml and the time (t2) until the swelled volume reaches 40 ml are determined. The same measurements are performed five times and an average value thereof is regarded as a measured value.

[Suu 1]

$$\text{Swelled volume(ml/g)} = \frac{\text{Bottom area of cylinder inside of cylinder with bottom plate(cm}^2)H(\text{cm})/\text{Specific gravity of physiological saline(cm}^3/\text{ml})}{\text{Weight of measuring sample(g)}}$$

The water-retention amount of the absorbent resin particle of the invention is, from the viewpoint of skin irritation resistance of an absorbent article, preferably 28 to 45 g/g, more preferably 32 to 40 g/g, and particularly preferably 34 to 38 g/g. The water-retention amount of the absorbent resin particle is measured by the following method.

<Measurement Method of Water-Retention Amount of the Absorbent Resin Particle>

A measuring sample (1.00 g) is placed in a tea bag (length: 20 cm, width: 10 cm) formed of a Nylon net having a mesh-opening of 63 m (JIS Z8801-1:2006). After the sample is immersed in 1,000 ml of physiological saline (sodium chloride concentration: 0.9% by weight) under no stirring for 1 hour, the bag is hung for 15 minutes for draining. Thereafter, the sample wrapped with the tea bag is placed in a centrifuge and is centrifuged at 150 G for 90 seconds to remove excessive physiological saline. Then, the weight (h1) including the tea bag is measured and the water-retention amount is determined according to the following equation. Herein, the temperature of the physiological saline and measuring atmosphere is set to 25 C 2 C.

The weight (h2) of the tea bag after the centrifugation is measured in the same manner as above except that the measuring sample is not used.

$$\text{Water-retention amount(g/g)} = (h1) - (h2)$$

The gel elastic modulus of thirtyfold swelled gel obtained by the absorption of 30 parts by weight of an artificial urine onto the absorbent resin particle is preferably 2,000 to 3,000 N/m$^2$, more preferably 2,025 to 2,950 N/m$^2$, particularly preferably 2,050 to 2,900 N/m$^2$, and most preferably 2,075 to 2,850 N/m$^2$. When the gel elastic modulus falls within such a range, a further excellent leakage resistance is exhibited when the absorbent resin particle is applied to an absorbent article. Herein, the gel elastic modulus (N/m$^2$) is a value determined by the following measurement method.

<Measurement Method of Gel Elastic Modulus>

An artificial urine [200 parts by weight of urea, 80 parts by weight of sodium chloride, 8 parts by weight of magnesium sulfate (7 hydrate), 3 parts by weight of calcium chloride (dihydrate), 2 parts by weight of ferric sulfate (7 hydrate), 9704 parts by weight of ion-exchange water] (60.0 g) was weighed out into a 100 ml beaker (inner diameter: 5 cm) and, in the same manner as the operations described in JIS K7224-1996, 2.0 g of a measuring sample was precisely weighed and charged into the above-described beaker to prepare a thirtyfold swelled gel.

The beaker containing the thirtyfold swelled gel was wrapped so that the swelled gel is not dried. After the beaker is allowed to stand under an atmosphere of 40 2 C for 3 hours and further under an atmosphere of 25 2 C for 0.5 hour, the wrapper is removed and the gel elastic modulus of the thirty-fold swelled gel is measured using a curd meter (for example, Curdmeter MAX ME-500 manufactured by K.K. Itec Techno Engineering). Herein, conditions for the curd meter are as follows.

Pressure-sensitive shaft: 8 mm
Spring: for 100 g
Load: 100 g
Elevation rate: 1 inch/7 seconds
Test property: breakage
Measurement time: 6 seconds
Measurement atmosphere temperature: 25 2 C The absorbent resin particle of the invention can be combined with a fibrous article to form an absorber. The structure of the absorber and the process for producing the same are the same as known ones {JP-A-2003-225565, JP-A-2006-131767, JP-A-2005-097569, etc.}. Moreover, it is preferable that the absorber constitutes absorbent articles {disposable diaper, sanitary napkin, etc.}. The process for producing the absorbent articles or likes are the same as known ones {JP-A-2003-225565, JP-A-2006-131767, JP-A-2005-097569, etc.}.

In the case where the absorbent resin particle of the invention is combined with a fibrous article to form an absorber, the weight ratio of the absorbent resin particle to the fiber (weight of absorbent resin particle/weight of fiber) is preferably 40/60 to 70/30 and more preferably 50/50 to 60/40.

EXAMPLES

Hereinafter, the present invention will be described in more detail by way of Examples and Comparative Examples. However, the invention is not necessarily limited thereto. Incidentally, "part(s)" means "part(s) by weight" and "%" means "% by weight" unless otherwise specified. The absorption amount of the absorbent resin particle determined by the measurement method of swelled volume, the water-retention amount, and the gel elastic modulus were measured by the aforementioned methods.

Example 1

155 parts (2.15 parts by mol) of a water-soluble vinyl monomer (a1-1) {acrylic acid, manufactured by Mitsubishi Chemical Corporation, purity 100%}, 0.6225 part (0.0024 part by mol) of a crosslinking agent (b1) {pentaerythritol triallyl ether, manufactured by Daiso Co., Ltd.}, and 340.27 parts of deionized water were maintained at 3 C under stirring and mixing. After nitrogen was introduced into the mixture to reduce a dissolved oxygen amount to 1 ppm or less, 0.62 part of a 1% aqueous hydrogen peroxide solution, 1.1625 parts of a 2% aqueous ascorbic acid solution, and 2.325 parts of a 2% aqueous 2,2'-azobis[2-methyl-N-(2-hydroxyethyl)-propionamide] solution were added and mixed to initiate polymerization. After the temperature of the mixture reached 90 C, polymerization was carried out at 90 2 C for about 5 hours to obtain a hydrogel (1).

Then, 128.42 parts of a 48.5% aqueous sodium hydroxide solution was added and mixed, while 502.27 parts of the hydrogel (1) was chopped in a mincing machine (12VR-400K manufactured by ROYAL Co.). Subsequently, 1.9 parts of a hydrophobic substance (C-1) {Mg stearate, volume-average particle diameter: 8 m} was added thereto and mixed to obtain a chopped gel (2). The chopped gel (2) was further dried in a through-flow band type dryer {150 C, wind velocity: 2 m/second} to obtain a dried form. After the dried form was pulverized in a juicing blender (OSTERIZER BLENDER manufactured by Oster Co.), a dried form particle was obtained by controlling the particle diameter to 150 to 710 m using sieves having sieve-openings of 150 m and 710 m. Under high-speed stirring (a high-speed stirring turbulizer manufactured by Hosokawa Micron Corporation; number of rotation: 2000 rpm) of 100 parts of the dried form particle, 5 parts of a 2% water/methanol mixed solution (weight ratio of water/methanol=70/30) of ethylene glycol diglycidyl ether was added by spraying and mixed and the mixture was allowed to stand at 150 C for 30 minutes to achieve surface crosslinking, thereby an absorbent resin particle (1) of the invention being obtained. The weight-average particle diameter of the absorbent resin particle (1) was 395 m and the apparent density was 0.58 g/ml. Also, the hydrophobic substance (C) was present in an amount of 0.980% in the inside of the absorbent resin particle (1) and the hydrophobic substance (C) was present in an amount of 0.020% on the surface of the absorbent resin particle (1).

Example 2

An absorbent resin particle (2) of the invention was obtained in the same manner as in Example 1 except that "1.9 parts of the hydrophobic substance (C-1)" was changed to "1.9 parts of the hydrophobic substance (C-2) {Ca stearate}". The weight-average particle diameter of the absorbent resin particle (2) was 390 m and the apparent density was 0.58 g/ml. Also, the hydrophobic substance (C) was present in an amount of 0.985% in the inside of the absorbent resin particle (2) and the hydrophobic substance (C) was present in an amount of 0.015% on the surface of the absorbent resin particle (2).

Example 3

An absorbent resin particle (3) of the invention was obtained in the same manner as in Example 1 except that "1.9 parts of the hydrophobic substance (C-1)" was changed to "1.9 parts of the hydrophobic substance (C-3) {Zn stearate}". The weight-average particle diameter of the absorbent resin particle (3) was 400 m and the apparent density was 0.58 g/ml. Also, the hydrophobic substance (C) was present in an amount of 0.970% in the inside of the absorbent resin particle (3) and the hydrophobic substance (C) was present in an amount of 0.030% on the surface of the absorbent resin particle (3).

Example 4

An absorbent resin particle (4) of the invention was obtained in the same manner as in Example 1 except that "1.9 parts of the hydrophobic substance (C-1)" was changed to "1.9 parts of the hydrophobic substance (C-4) {Al stearate}". The weight-average particle diameter of the absorbent resin particle (4) was 395 m and the apparent density was 0.58 g/ml. Also, the hydrophobic substance (C) was present in an amount of 0.950% in the inside of the absorbent resin particle (4) and the hydrophobic substance (C) was present in an amount of 0.050% on the surface of the absorbent resin particle (4).

Example 5

An absorbent resin particle (5) of the invention was obtained in the same manner as in Example 1 except that "1.9 parts of the hydrophobic substance (C-1)" was changed to "0.19 part of the hydrophobic substance (C-1)". The weight-average particle diameter of the absorbent resin particle (5) was 405 m and the apparent density was 0.60 g/ml.

Also, the hydrophobic substance (C) was present in an amount of 0.099% in the inside of the absorbent resin particle (5) and the hydrophobic substance (C) was present in an amount of 0.001% on the surface of the absorbent resin particle (5).

Example 6

An absorbent resin particle (6) of the invention was obtained in the same manner as in Example 1 except that "1.9 parts of the hydrophobic substance (C-1)" was changed to "9.5 parts of the hydrophobic substance (C-1)". The weight-average particle diameter of the absorbent resin particle (6) was 395 m and the apparent density was 0.58 g/ml.

Also, the hydrophobic substance (C) was present in an amount of 4.950% in the inside of the absorbent resin particle (6) and the hydrophobic substance (C) was present in an amount of 0.050% on the surface of the absorbent resin particle (6).

Example 7

An absorbent resin particle (7) of the invention was obtained in the same manner as in Example 1 except that "sieves having sieve-openings of 150 m and 710 m" was changed to "sieves having sieve-openings of 150 m and 850 m" to control the particle diameter to 150 m to 850 m. The weight-average particle diameter of the absorbent resin particle (7) was 540 m and the apparent density was 0.57 g/ml. Also, the hydrophobic substance (C) was present in an amount of 0.985% in the inside of the absorbent resin particle (7) and the hydrophobic substance (C) was present in an amount of 0.015% on the surface of the absorbent resin particle (7).

Example 8

An absorbent resin particle (8) of the invention was obtained in the same manner as in Example 1 except that "sieves having sieve-openings of 150 m and 710 m" was changed to "sieves having sieve-openings of 150 m and 600 m" to control the particle diameter to 150 m to 600 m. The weight-average particle diameter of the absorbent resin particle (8) was 300 m and the apparent density was 0.60 g/ml. Also, the hydrophobic substance (C) was present in an amount of 0.980% in the inside of the absorbent resin particle (8) and the hydrophobic substance (C) was present in an amount of 0.020% on the surface of the absorbent resin particle (8).

Example 9

An absorbent resin particle (9) of the invention was obtained in the same manner as in Example 1 except that "1.9 parts of the hydrophobic substance (C-1)" was changed to "0.95 part of the hydrophobic substance (C-5) {stearic acid}". The weight-average particle diameter of the absorbent resin particle (9) was 395 m and the apparent density was 0.58 g/ml. Also, the hydrophobic substance (C) was present in an amount of 0.490% in the inside of the absorbent resin particle (9) and the hydrophobic substance (C) was present in an amount of 0.010% on the surface of the absorbent resin particle (9).

Example 10

An absorbent resin particle (10) of the invention was obtained in the same manner as in Example 1 except that "1.9 parts of the hydrophobic substance (C-1)" was changed to "0.19 part of the hydrophobic substance (C-5) and 0.95 part of Mg hydroxide". The weight-average particle diameter of the absorbent resin particle (10) was 405 m and the apparent density was 0.58 g/ml. Also, the hydrophobic substance (C) was present in an amount of 0.475% in the inside of the absorbent resin particle (10) and the hydrophobic substance (C) was present in an amount of 0.025% on the surface of the absorbent resin particle (10).

Example 11

An absorbent resin particle (11) of the invention was obtained in the same manner as in Example 1 except that 0.6 part of a hydrophilic inorganic particle (d-1) {Aerosil 200PE (a product manufactured by Nippon Aerosil Co., Ltd.)} was added after the surface crosslinking. The weight-average particle diameter of the absorbent resin particle (11) was 390 m and the apparent density was 0.57 g/ml. Also, the hydrophobic substance (C) was present in an amount of 0.980% in the inside of the absorbent resin particle (11) and the hydrophobic substance (C) was present in an amount of 0.020% on the surface of the absorbent resin particle (11).

Example 12

An absorbent resin particle (12) of the invention was obtained in the same manner as in Example 1 except that "155 parts (2.15 parts by mol) of a water-soluble vinyl monomer (a1-1), 0.6225 part (0.0024 part by mol) of a crosslinking agent (b1), and 340.27 parts by weight of deionized water" was changed to "155 parts (2.15 parts by mol) of a water-soluble vinyl monomer (a1-1), (0.0024 part by mol) of a crosslinking agent (b1), 1.55 part of a hydrophobic substance (C-1), and 335.541 parts by weight of deionized water", "502.27 parts of the hydrogel (1)" was changed to "500.46 parts of the hydrogel (1)", "128.42 parts of a 48.5% aqueous sodium hydroxide solution" was changed to "127.84 parts of a 48.5% aqueous sodium hydroxide solution", and the hydrophobic substance (C-1) was not used in the crushing process of the hydrogel. The weight-average particle diameter of the absorbent resin particle (12) was 395 m and the apparent density was 0.59 g/ml. Also, the hydrophobic substance (C) was present in an amount of 0.810% in the inside of the absorbent resin particle (12) and the hydrophobic substance (C) was present in an amount of 0.010% on the surface of the absorbent resin particle (12).

Example 13

An absorbent resin particle (13) of the invention was obtained in the same manner as in Example 1 except that "1.9 parts of the hydrophobic substance (C-1)" was changed to "3.8 parts of the hydrophobic substance (C-6) {sorbitol monostearate}". The weight-average particle diameter of the absorbent resin particle (13) was 395 m and the apparent density was 0.58 g/ml. Also, the hydrophobic substance (C) was present in an amount of 1.990% in the inside of the absorbent resin particle (13) and the hydrophobic substance (C) was present in an amount of 0.010% on the surface of the absorbent resin particle (13).

Example 14

An absorbent resin particle (14) of the invention was obtained in the same manner as in Example 1 except that "1.9 parts of the hydrophobic substance (C-1)" was changed to "3.8 parts of the hydrophobic substance (C-7) {sucrose monostearate}". The weight-average particle diameter of the absorbent resin particle (14) was 395 m and the apparent density was 0.58 g/ml. Also, the hydrophobic substance (C) was present in an amount of 1.950% in the inside of the absorbent resin particle (14) and the hydrophobic substance (C) was present in an amount of 0.050% on the surface of the absorbent resin particle (14).

Example 15

An absorbent resin particle (15) of the invention was obtained in the same manner as in Example 1 except that "1.9 parts of the hydrophobic substance (C-1)" was changed to "1.9 parts of the hydrophobic substance (C-8) {N-ethyldioctadecanamide}". The weight-average particle diameter of the absorbent resin particle (15) was 395 m and the apparent density was 0.58 g/ml. Also, the hydrophobic substance (C) was present in an amount of 0.985% in the inside of the absorbent resin particle (15) and the hydrophobic substance (C) was present in an amount of 0.015% on the surface of the absorbent resin particle (15).

Example 16

An absorbent resin particle (16) of the invention was obtained in the same manner as in Example 1 except that "1.9 parts of the hydrophobic substance (C-1)" was changed to "1.9 parts of the hydrophobic substance (C-9) {N-octylheptaconamide}". The weight-average particle diameter of the absorbent resin particle (16) was 395 m and the apparent density was 0.58 g/ml. Also, the hydrophobic substance (C) was present in an amount of 1.950% in the inside of the absorbent resin particle (16) and the hydrophobic substance (C) was present in an amount of 0.050% on the surface of the absorbent resin particle (16).

Example 17

An absorbent resin particle (17) of the invention was obtained in the same manner as in Example 1 except that "1.9 parts of the hydrophobic substance (C-1)" was changed to "0.95 part of the hydrophobic substance (C-10) {stearyl alcohol}". The weight-average particle diameter of the absorbent resin particle (17) was 395 m and the apparent density was 0.58 g/ml. Also, the hydrophobic substance (C) was present in an amount of 0.490% in the inside of the absorbent resin particle (17) and the hydrophobic substance (C) was present in an amount of 0.010% on the surface of the absorbent resin particle (17).

Comparative Example 1

To 40 parts of clay (LAPONI PE XLG: manufactured by ROCKWOOD ADDITIVES LIMITED Co.) was added a solution obtained by dissolving 0.004 part of an amino-modified silicone (KF354: a product manufactured by Shin-Etsu Chemical Co., Ltd.) as the hydrophobic substance (C) in parts of methanol. After stirring at 25 C for 2 minutes, drying was performed at 60 C for 1 hour to obtain a material particle (E). The volume-average particle diameter of the material particle (E) was 80 m.

Then, into a glass-made reaction vessel were charged 77 parts of sodium acrylate, 22.85 parts of acrylic acid, 0.15 part of N,N'-methylenebisacrylamide, 293 parts of deionized water, and 0.001 part of dichlorotris(triphenylphosphine)ruthenium, and the temperature of the content was kept at 3 C under stirring and mixing. After nitrogen was introduced into the content to reduce a dissolved oxygen amount to 1 ppm or less, 0.3 part of a 1% aqueous hydrogen peroxide solution, 0.8 part of a 0.2% aqueous ascorbic acid solution, and 0.8 part of a 2% aqueous solution of 2,2'-azobisamidinopropane dihydrochloride were added and mixed to initiate polymerization. After the temperature of the reaction solution reached 80 C, polymerization was carried out at a polymerization temperature of 80 2 C for about 5 hours to obtain a hydrogel (1).

To 300 parts of the hydrogel (1) were added 30 parts of the material particle (E) and 0.3 part of a surfactant (1) (Sanmolin OT70 manufactured by Sanyo Chemical Industries, Ltd.), and the mixture was kneaded in a mincing machine (12VR- 400K manufactured by Iizuka Kogyo K.K., hole diameter of catch basin: 6 mm) at 25 C for 5 minutes. Then, the kneaded mixture was dried in a through-flow band type dryer under conditions of 135 C and a wind velocity of 2.0 m/second to obtain a dried polymer.

After the dried polymer was pulverized in a juicing blender (OSTERIZER BLENDER manufactured by Oster Co.) and was controlled to a particle diameter of 150 to 710 m using sieves having sieve-openings of 150 m and 710 m. Under high-speed stirring (a high-speed stirring turbulizer manufactured by Hosokawa Micron Corporation; number of rotation: 2000 rpm) of 100 parts of the pulverized dried polymer, 2 parts of a 10% water/methanol mixed solution (weight ratio of water/methanol=70/30) of ethylene glycol diglycidyl ether was added by spraying and mixed and the mixture was allowed to stand at 140 C for 30 minutes to achieve crosslinking, thereby an absorbent resin particle (H1) for comparison being obtained. The weight-average particle diameter of the absorbent resin particle (H1) was 395 m and the apparent density was 0.55 g/ml. Also, the hydrophobic substance (C) was present in an amount of 0.005% in the inside of the absorbent resin particle (H1) and the hydrophobic substance (C) was not present on the surface of the absorbent resin particle (H1).

Comparative Example 2

An absorbent resin particle (H2) for comparison was obtained in the same manner as in Comparative Example 1 except that "30 parts of the material particle (E)" was changed to "3 parts of silicone beads (Tospearl manufactured by Toshiba Silicone Co., Ltd.; average particle diameter: 2 m)" and "0.3 part of a surfactant (1) (Sanmolin OT70 manufactured by Sanyo Chemical Industries, Ltd.)" was changed to "0.3 part of a surfactant (2) (Naroacty ID50 manufactured by Sanyo Chemical Industries, Ltd.)". The weight-average particle diameter of the absorbent resin particle (H2) was 400 m and the apparent density was 0.55 g/ml. Also, the hydrophobic substance (C) was not present on the surface of the absorbent resin particle (H2) and was only present in the inside thereof.

Comparative Example 3

155 parts (2.15 parts by mol) of a water-soluble vinyl monomer (a1-1) {acrylic acid, manufactured by Mitsubishi Chemical Corporation, purity 100%}, 0.6225 part (0.0024 part by mol) of a crosslinking agent (b1) {pentaerythritol triallyl ether, manufactured by Daiso Co., Ltd.}, and 340.27 parts of deionized water were maintained at 3 C under stirring and mixing. After nitrogen was introduced into the mixture to reduce a dissolved oxygen amount to 1 ppm or less, 0.62 part of a 1% aqueous hydrogen peroxide solution, 1.1625 parts of a 2% aqueous ascorbic acid solution, and 2.325 parts of a 2% aqueous 2,2'-azobis[2-methyl-N-(2-hydroxyethyl)-propionamide] solution were added and mixed to initiate polymerization. After the temperature of the mixture reached 90 C, polymerization was carried out at 90 2 C for about 5 hours to obtain a hydrogel (1). Then, 128.42 parts of a 48.5% aqueous sodium hydroxide solution was added and mixed, while 502.27 parts of the hydrogel (1) was chopped in a mincing machine (12VR-400K manufactured by ROYAL Co.), thereby a chopped gel (2) being obtained. The chopped gel (2) was further dried in a through-flow band type dryer {150 C, wind velocity: 2 m/second} to obtain a dried form. After the dried form was pulverized in a juicing blender (OSTERIZER BLENDER manufactured by Oster Co.), a dried form particle was obtained by controlling the particle diameter to 150 m to 710 m using sieves having sieve-openings of 150 m and 710 m. Under high-speed stirring (a high-speed stirring turbulizer manufactured by Hosokawa Micron Corporation; number of rotation: 2000 rpm) of 100 parts of the dried form particle, 5 parts of a 2% water/methanol mixed solution (weight ratio of water/methanol=70/30) of ethylene glycol diglycidyl ether was added by spraying and mixed and the mixture was allowed to stand at 150 C for 30 minutes to achieve surface crosslinking, thereby an absorbent resin particle (H3) for comparison being obtained. The weight-average particle diameter of the absorbent resin particle (H3) was 405 m and the apparent density was 0.61 g/ml. Also, the hydrophobic substance (C) was not present in the inside of the absorbent resin particle (H3) and on the surface thereof.

Comparative Example 4

An absorbent resin particle (H4) for comparison was obtained in the same manner as in Comparison Example 1 except that 1.0 part of the hydrophobic substance (C-1) was mixed after surface crosslinking. The weight-average particle diameter of the absorbent resin particle (H4) was 400 m and the apparent density was 0.61 g/ml. Also, the hydrophobic substance (C) was not present in the inside of the absorbent resin particle (H4) and was present in an amount of 1.000% on the surface thereof.

Comparative Example 5

An absorbent resin particle (H5) for comparison was obtained according to Example 1 of JP-A-2007-291351. The weight-average particle diameter of the absorbent resin particle (H5) was 400 m and the apparent density was 0.70 g/ml. Also, the hydrophobic substance (C) was not present in the inside of the absorbent resin particle (H4) and on the surface thereof.

Comparative Example 6

An absorbent resin particle (H6) for comparison was obtained in the same manner as in Comparison Example 4 except that 0.05 part of the hydrophobic substance (C-1) was mixed beforehand to effect surface crosslinking and any hydrophobic substance was not added after the surface crosslinking. The weight-average particle diameter of the absorbent resin particle (H6) was 400 m and the apparent density was 0.61 g/ml. Also, the hydrophobic substance (C) was not present in the inside of the absorbent resin particle (H4) and was present in an amount of 1.000% on the surface thereof.

Figure 2:
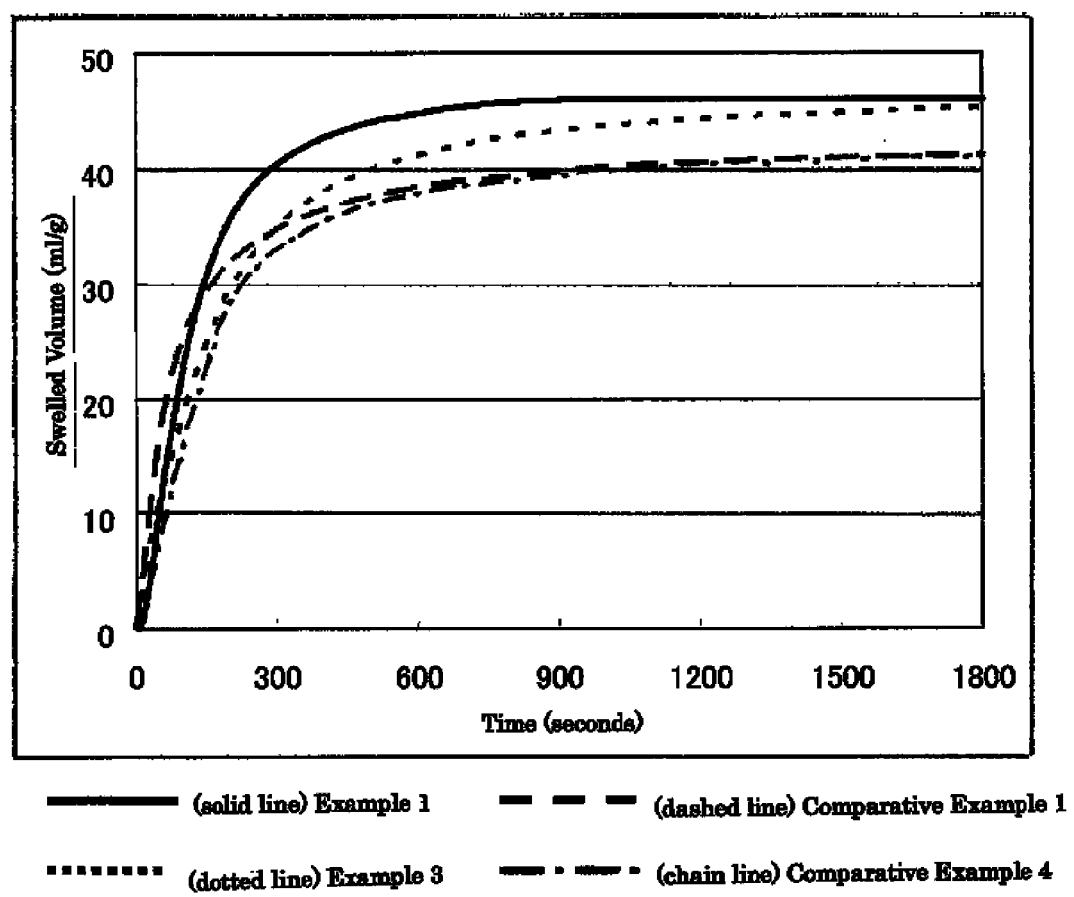
FIG. 2 shows measurement results of the absorbent resin particles obtained in Example 1 and Comparative Examples 1, 3, and 4 by a measurement method of swelled volume (until 1800 seconds).

Results of measurement on the absorbent resin particles obtained in Example 1 and Comparative Examples 1, 3, and 4 by the measurement method of swelled volume are shown in FIG. 1 and FIG. 2. Incidentally, the distance of elevation of the disk was measured using a digimatic indicator ID-F150 manufactured by Mitutoyo Co.

As is understood from FIG. 1 and FIG. 2, the absorption rate pattern of the absorbent resin particle of Example 1 describes a sigmoid absorption rate curve where the rate is slow in the early stage, moderate in the middle stage, and fast in the late stage.

With regard to the absorbent resin particles obtained in Examples 1 to 17 and Comparative Examples 1 to 6, measured physical properties {weight-average particle diameter, apparent density} and performance evaluation results {time until the particle reaches a specific swelled volume by the measurement method of swelled volume, water-retention amount, gel elastic modulus} are shown in Tables 1 and 2.

TABLE 1

| | | Example | | | | | | | | |
|---|---|---|---|---|---|---|---|---|---|---|
| | | 1 | 2 | 3 | 4 | 5 | 6 | 7 | 8 | 9 |
| t1 | (second) | 31 | 33 | 30 | 41 | 23 | 36 | 38 | 28 | 28 |
| t2 | (second) | 290 | 270 | 295 | 430 | 413 | 502 | 420 | 270 | 500 |
| t2/t1 | | 9.4 | 8.2 | 9.8 | 10.5 | 18.0 | 13.9 | 11.1 | 9.6 | 17.9 |
| Weight-average particle diameter | (m) | 395 | 390 | 400 | 395 | 405 | 395 | 540 | 300 | 395 |
| Apparent density | (g/ml) | 0.58 | 0.58 | 0.58 | 0.58 | 0.6 | 0.58 | 0.57 | 0.6 | 0.58 |
| Water-retention amount | (g/g) | 36 | 36 | 35 | 36 | 36 | 37 | 36 | 35 | 36 |
| Gel strength | (kN/m$^2$) | 2.3 | 2.4 | 2.3 | 2.3 | 2.5 | 2.4 | 2.5 | 2.3 | 2.4 |

| | | Example | | | | | | | |
|---|---|---|---|---|---|---|---|---|---|
| | | 10 | 11 | 12 | 13 | 14 | 15 | 16 | 17 |
| t1 | (second) | 41 | 26 | 32 | 35 | 38 | 44 | 39 | 31 |
| t2 | (second) | 390 | 270 | 373 | 280 | 352 | 486 | 382 | 290 |
| t2/t1 | | 9.5 | 10.4 | 11.7 | 8.0 | 9.3 | 11 | 9.8 | 9.4 |
| Weight-average particle diameter | (m) | 405 | 390 | 395 | 395 | 395 | 400 | 395 | 395 |
| Apparent density | (g/ml) | 0.58 | 0.57 | 0.59 | 0.59 | 0.57 | 0.6 | 0.58 | 0.58 |
| Water-retention amount | (g/g) | 36 | 37 | 36 | 36 | 37 | 35 | 35 | 36 |
| Gel strength | (kN/m$^2$) | 2.3 | 2.4 | 2.3 | 2.4 | 2.3 | 2.4 | 2.3 | 2.4 |

TABLE 2

| | | Comparative Example | | | | | |
|---|---|---|---|---|---|---|---|
| | | 1 | 2 | 3 | 4 | 5 | 6 |
| t1 | (second) | 14 | 12 | 19 | 40 | 24 | 45 |
| t2 | (second) | 980 | 483 | 514 | 1100 | 1348 | 1623 |
| t2/t1 | | 70 | 40.3 | 27.1 | 27.5 | 56.2 | 36.1 |
| Weight-average particle diameter | (m) | 395 | 400 | 405 | 400 | 400 | 395 |
| Apparent density | (g/ml) | 0.55 | 0.55 | 0.61 | 0.61 | 0.7 | 0.6 |
| Water-retention amount | (g/g) | 36 | 35 | 36 | 36 | 50 | 35 |
| Gel strength | (kN/m$^2$) | 2.1 | 2.2 | 2.1 | 2.2 | 1.6 | 2.1 |

As is understood from Tables 1 and 2, the absorbent resin particles of the invention (Examples 1 to 17) have suitable absorption rate patterns as compared with the absorbent resin particles of Comparative Examples 1 to 6. From the comparison between the absorbent resin particles of the invention (Examples 1 to 17) and the absorbent resin particles of Comparative Examples 4 and 6, it is understood that suitable absorption patterns are obtained by the presence of a hydrophobic substance in the inside of the particle and on the surface thereof.

Subsequently, there are evaluated absorption characteristics to be shown when the absorbent resin particles are applied to absorbent articles in the case where the particles have suitable absorption rate patterns. Using absorbent resin particles obtained in Examples 1 to 17 and Comparative Examples 1 to 6, an absorbent article (disposable diaper) was prepared as follows and a surface dryness value was evaluated by the SDME method. The results are shown in Tables 3 and 4.

<Preparation of Absorbent Article (Disposable Diaper) 1>

After 100 parts of fluff pulp and 100 parts of an evaluating sample {absorbent resin particle} were mixed in an air-flow type mixing apparatus {a pad former manufactured by K.K. O-TEC} to obtain a mixture, the mixture was uniformly laminated on an acryl plate (thickness: 4 mm) so as to be a basis weight of about 500 g/m$^2$ and was then pressed under a pressure of 5 kg/cm$^2$ for 30 seconds to obtain an absorber (1).

The absorber (1) was cut into a rectangle having a size of 10 cm 40 cm, a water-absorbing paper (basis weight: 15.5 g/m², manufactured by Advantec Co., filter paper No. 2) having the same size as that of the absorber were disposed on the upside and back side of the absorber, further a polyethylene sheet (a polyethylene film UB-1 manufactured by Tamapoly Co., Ltd.) was disposed on the back side, and a non-woven fabric (basis weight: 20 g/m², Eltas Guard manufactured by Asahi Kasei Corporation) was disposed on the surface, thereby a disposable diaper (1) being prepared. The weight ratio of the absorbent resin particle to fiber (weight of absorbent resin particle/weight of fiber) was 50/50.

<Preparation of Absorbent Article (Disposable Diaper) 2>

A disposable diaper (2) was prepared in the same manner as in Preparation of Absorbent Article (Disposable Diaper) 1 except that "100 parts of fluff pulp and 100 parts of an evaluating sample {absorbent resin particle}" was changed to "80 parts of fluff pulp and 120 parts of an evaluating sample {absorbent resin particle}". The weight ratio of the absorbent resin particle to fiber (weight of absorbent resin particle/weight of fiber) was 60/40.

<Surface Dryness Value by SDME Method>

A detector of an SDME (Surface Dryness Measurement Equipment) tester (manufactured by WK system Co.) was placed on a fully wet disposable diaper {prepared by immersing a disposable diaper in an artificial urine (0.03% by weight of potassium chloride, 0.08% by weight of magnesium sulfate, 0.8% by weight of sodium chloride, and 99.09% by weight of deionized water) and allowing the diaper to stand for 60 minutes} to set a 0% dryness value and then, the detector of the SDME tester was placed on a dry disposable diaper {prepared by drying a disposable diaper under heating at 80 C for 2 hours} to set a 100% dryness value, thereby calibration of the SDME tester being performed. Then, a metal ring (inner diameter: 70 mm, length: 50 mm) was set on the center of the disposable diaper to be measured and 80 ml of the artificial urine was injected thereto. When the artificial urine was completely absorbed {until the gloss by the artificial urine was not confirmed}, the metal ring was immediately removed and three detectors of the SDME tester were placed on the center of the disposable diaper and on the left side and right side thereof {3 positions at equal intervals of 10 cm from the end of the disposable diaper having a length of 40 cm}. Then, measurement of surface dryness values was started and the values after 5 minutes from the start of the measurement were indicated as SD1-1 {center}, SD1-2 {left}, and SD1-3 {right}.

Incidentally, the measurement was performed, wherein the artificial urine, the measuring atmosphere, and the standing atmosphere were 25 5 C and 65 10% RH.

TABLE 4

| | | | Comparative Example | | | | | |
|---|---|---|---|---|---|---|---|---|
| | | | 1 | 2 | 3 | 4 | 5 | 6 |
| Disposable Diaper (1) | SD1-1 | (%) | 57 | 96 | 79 | 89 | 68 | 80 |
| | SD1-2 | (%) | 98 | 53 | 64 | 54 | 57 | 62 |
| | SD1-3 | (%) | 98 | 54 | 65 | 52 | 57 | 60 |
| Disposable Diaper (2) | SD1-1 | (%) | 55 | 96 | 80 | 90 | 70 | 78 |
| | SD1-2 | (%) | 96 | 50 | 65 | 48 | 57 | 62 |
| | SD1-3 | (%) | 95 | 54 | 60 | 50 | 56 | 61 |

As is understood from Tables 3 and 4, the absorbent articles using the absorbent resin particles of the invention show no unevenness in SD1-1, SD1-2, and SD1-3 and thus are excellent as compared with the absorbent articles using the absorbent resin particles for comparison. That is, since the absorbent resin particles of the invention have specific absorption rate patterns when applied to absorbent articles, they show excellent absorption characteristics. Therefore, it is easily expected that there is no fear of skin irritation or the like even when absorbent articles employing the absorbent resin particles of the invention are used.

INDUSTRIAL APPLICABILITY

The absorbent resin particle of the present invention can be applied to absorbers containing an absorbent resin particle and a fibrous material, and is useful for absorbent articles comprising the absorbers {a disposable diaper, a sanitary napkin, and a medical blood-retention agent}. Also, the absorbent resin particle can be employed for various applications such as a pet urine-absorbing agent, a urine-gelling agent for portable toilet, a freshness-retaining agent for vegetables and fruits, a drip-absorbing agent for meat and fish, a cold-storing agent, a disposable pocket warmer, a gelling agent for batteries, a water-retention agent for plants and soil, an anti-dewing agent, a water-sealing agent, a packing agent, and artificial snow.

| | [Description of Reference Numerals and Signs] |
|---|---|
| 1 | cylinder with bottom plate |
| 2 | disk with handgrip |
| 3 | absorbent resin particle |
| 4 | thickness displaying part of digimatic indicator |
| 5 | rod of digimatic indicator for thickness measurement |
| 6 | platform of digimatic indicator |

TABLE 3

| | | | Example | | | | | | | | | | | | | | | | |
|---|---|---|---|---|---|---|---|---|---|---|---|---|---|---|---|---|---|---|---|
| | | | 1 | 2 | 3 | 4 | 5 | 6 | 7 | 8 | 9 | 10 | 11 | 12 | 13 | 14 | 15 | 16 | 17 |
| Disposable Diaper (1) | SD1-1 | (%) | 80 | 82 | 81 | 90 | 74 | 90 | 90 | 70 | 80 | 92 | 75 | 83 | 84 | 79 | 72 | 79 | 75 |
| | SD1-2 | (%) | 89 | 86 | 84 | 73 | 80 | 72 | 80 | 83 | 82 | 79 | 98 | 81 | 92 | 89 | 85 | 82 | 82 |
| | SD1-3 | (%) | 89 | 86 | 84 | 73 | 80 | 72 | 80 | 83 | 82 | 79 | 98 | 81 | 90 | 91 | 85 | 85 | 86 |
| Disposable Diaper (2) | SD1-1 | (%) | 79 | 81 | 80 | 89 | 75 | 88 | 88 | 72 | 81 | 90 | 72 | 85 | 82 | 79 | 70 | 74 | 77 |
| | SD1-2 | (%) | 90 | 84 | 85 | 75 | 77 | 74 | 83 | 81 | 81 | 80 | 97 | 79 | 90 | 89 | 84 | 80 | 84 |
| | SD1-3 | (%) | 90 | 84 | 85 | 75 | 77 | 74 | 83 | 81 | 81 | 80 | 97 | 79 | 91 | 91 | 83 | 82 | 83 |

The invention claimed is:

1. An absorbent resin particle comprising a crosslinked polymer (A1) including, as an essential constituent unit:
   at least one of a water-soluble vinyl monomer (a1) and a hydrolyzable vinyl monomer (a2); and
   a crosslinking agent (b),
   wherein, in a measurement method of swelled volume per 1 g of the absorbent resin particle against physiological saline, a ratio (t2/t1) of the time (t2) until swelled volume reaches 40 ml to the time (t1) until the swelled volume reaches 5 ml is 5 to 20.

2. The absorbent resin particle according to claim 1, wherein the time (t1) until the swelled volume reaches 5 ml is 20 to 60 seconds.

3. The absorbent resin particle according to claim 1, which further comprises a hydrophobic substance (C).

4. The absorbent resin particle according to claim 3, wherein the content of the hydrophobic substance (C) in the inside of the absorbent resin particle is 0.01 to 10.0% by weight based on the weight of the crosslinked polymer (A1).

5. The absorbent resin particle according to claim 3, wherein the content of the hydrophobic substance (C) present on the surface of the absorbent resin particle is 0.001 to 1.0% by weight based on the weight of the crosslinked polymer (A1).

6. The absorbent resin particle according to claim 3, wherein the hydrophobic substance (C) is at least one selected from the group consisting of fatty acid esters, fatty acids and salts thereof, aliphatic alcohols, and long chain aliphatic amides.

7. The absorbent resin particle according to claim 6, wherein the hydrophobic substance (C) is at least one selected from the group consisting of sorbitol stearate ester, sucrose stearate ester, stearic acid, Mg stearate, Ca stearate, Zn stearate, and Al stearate.

8. The absorbent resin particle according to claim 7, wherein the hydrophobic substance (C) is a sucrose stearate ester or Mg stearate.

9. The absorbent resin particle according to claim 1, which has an indeterminate crushed shape.

10. The absorbent resin particle according to claim 1, which further comprise an inorganic powder (D) attached on the surface thereof in an amount of 0.01 to 3.0% based on the weight of the crosslinked polymer (A1).

11. The absorbent resin particle according to claim 1, which has an apparent density of 0.54 to 0.70 g/ml.

12. The absorbent resin particle according to claim 1, wherein a gel elastic modulus of a thirtyfold swelled gel obtained after 1 part by weight of the absorbent resin particle absorbs 30 parts by weight of an artificial urine is 2,000 to 3,000 $N/m^2$.

13. An absorber comprising the absorbent resin particle according to claim 1 and a fibrous material.

14. An absorbent article comprising the absorber according to claim 13.

15. A process for producing an absorbent resin particle comprising:
   a step of mixing and/or kneading a hydrophobic substance (C) with a hydrogel of a crosslinked polymer (A1) including, as an essential constituent unit, a water-soluble vinyl monomer (a1) and/or a hydrolyzable vinyl monomer (a2) and an internal crosslinking agent (b); and/or
   a step of obtaining a hydrogel of a crosslinked polymer (A1) by polymerizing a water-soluble vinyl monomer (a1) and/or a hydrolyzable vinyl monomer (a2) and an internal crosslinking agent (b) as an essential constituent unit under an acidic conduction in the presence of a hydrophobic substance (C),
   wherein, in a measurement method of swelled volume per 1 g of the absorbent resin particle against physiological saline, a ratio (t2/t1) of the time (t2) until swelled volume reaches 40 ml to the time (t1) until the swelled volume reaches 5 ml is 5 to 20.

* * * * *